(12) United States Patent
Schmittgen

(10) Patent No.: US 8,192,938 B2
(45) Date of Patent: Jun. 5, 2012

(54) METHODS FOR QUANTIFYING MICRORNA PRECURSORS

(75) Inventor: Thomas D. Schmittgen, Granville, OH (US)

(73) Assignee: The Ohio State University, Columbus, OH (US)

(*) Notice: Subject to any disclaimer, the term of this patent is extended or adjusted under 35 U.S.C. 154(b) by 431 days.

(21) Appl. No.: 11/816,767

(22) PCT Filed: Feb. 24, 2006

(86) PCT No.: PCT/US2006/006800
§ 371 (c)(1), (2), (4) Date: Aug. 21, 2007

(87) PCT Pub. No.: WO2007/044057
PCT Pub. Date: Apr. 19, 2007

(65) Prior Publication Data
US 2009/0123917 A1 May 14, 2009

Related U.S. Application Data

(60) Provisional application No. 60/656,109, filed on Feb. 24, 2005.

(51) Int. Cl.
*C12Q 1/68* (2006.01)
*C12P 19/34* (2006.01)

(52) U.S. Cl. ........................ 435/6.12; 435/91.2

(58) Field of Classification Search .................. None
See application file for complete search history.

(56) References Cited

U.S. PATENT DOCUMENTS

| 6,117,635 | A * | 9/2000 | Nazarenko et al. ............. 435/6 |
| 6,179,635 | B1 | 1/2001 | Wang |
| 6,974,672 | B2 | 12/2005 | Powers et al. |
| 2004/0152112 | A1 | 8/2004 | Croce et al. |
| 2005/0020525 | A1 | 1/2005 | McSwiggen et al. |
| 2005/0059005 | A1 | 3/2005 | Tuschl et al. |
| 2005/0144669 | A1 | 6/2005 | Bartel et al. |
| 2005/0182005 | A1 | 8/2005 | Landthaler et al. |
| 2005/0221293 | A1 | 10/2005 | Pfeffer et al. |
| 2005/0222399 | A1 | 10/2005 | Bentwich |
| 2005/0227934 | A1 | 10/2005 | Poy et al. |
| 2005/0266418 | A1 | 12/2005 | Chen et al. |
| 2005/0266443 | A1 | 12/2005 | Croce et al. |
| 2005/0277139 | A1 | 12/2005 | Bentwich et al. |
| 2006/0003322 | A1 | 1/2006 | Bentwich |
| 2006/0019286 | A1 | 1/2006 | Horvitz et al. |
| 2006/0236427 | A1 * | 10/2006 | Chiang et al. ............. 800/284 |

FOREIGN PATENT DOCUMENTS

| FR | 2861086 | 4/2005 |
| WO | 2005/019453 | 3/2005 |
| WO | 2005/040419 | 5/2005 |
| WO | 2005/042705 | 5/2005 |
| WO | 2005/054494 | 6/2005 |
| WO | 2005/092393 | 10/2005 |
| WO | 2007/044057 | 4/2007 |

OTHER PUBLICATIONS

Schmittgen et al. A high-throughput method to monitor the expression of microRNA precursors. Nucleic Acids Res. (2004) vol. 32, No. 4, e43, pp. 1-10.*
Liu et al. An oligonucleotide microchip for genome-wide microRNA profiling in human and mouse tissues. Proc. Natl. Acad. Sci. USA (2004) vol. 101, No. 26, pp. 9740-9744.*
Paddison et al. Cloning of short hairpin RNAs for gene knockdown in mammalian cells. Nature Methods (2004) vol. 1, No. 2, pp. 163-167.*
International Search Report and Written Opinion from PCT/US06/06800, mailed Sep. 25, 2007.
Ambros et al., "A uniform system for microRNA annotation", RNA, 2003, 9 (3) pp. 277-279.
Chen et al., Applied Biosystems, MicroRNA Quantitation by Looped RT-PCR, one page brochure, 2004, 127PR05-01.
Calin et al, "Frequent deletions and down-regulation of micro-RNA genes miR15 and miR16 at 13q14 in chronic lymphocytic leukemia", Proc Natl Acad Sci, USA, 99 (24), pp. 15524-15529, 2002.
Calin et al., "MicroRNA profiling reveals distinct signatures in B cell chronic lymphocytic leukemias", Medical Sciences, PNAS< Aug. 10, 2004, vol. 101, No. 32, pp. 17555-11760.
Chen et al., "Real-time quantification of microRNAs by stem-loop RT-PCR", Nucleic Acids Res., vol. 33, No. 20, 9 pgs., 2005.
Eisen et al., "Cluster analysis and display of genome-wide expression patterns", Proc Natl Acad Sci USA, 1998, 95 (25) pp. 14863-14868.
Griffiths-Jones, "The MicroRNA Registry", Nucleic Acids Res, 2004, 32 (1): pp. D109-D111.
Hutvagner et al., "A cellular function for the RNA-interference enzyme Dicer in the maturation of the let-7 small temporal RNA", Science, 2001, 293 (5531), pp. 834-838.
Hutvagner et al., "A microRNA in a multiple-turnover RNai enzyme complex", Science, 2002, 197 (5589), pp. 2056-2060.
Jiang et al., "Real-time epxression profiling of microRNA precursors in human cancer cell lines", Nucleic Acid Res., vol. 33, No. 17, pp. 5394-5403, 2005.
Jiang et al., "Association of MicroRNA Expression in Hepatocellular Carcinomas with Hepatitis Infection, Cirrhosis, and Patient Survival", Clin Cancer Res. 14 (2), pp. 419-427, Jan. 15, 2008.
Ketting et al., "Dicer functions in RNA interference and in synthesis of small RNA involved in developmental timing in C elegans", Genes Dev, 2001, 15 (20) pp. 2654-2659.
Lagos-Quintana, et al., "Identification of novel genes coding for small expressed RNAs", Science, 2001, 294 (5543) pp. 853-858.

(Continued)

*Primary Examiner* — Kenneth R. Horlick
*Assistant Examiner* — David Thomas
(74) *Attorney, Agent, or Firm* — Calfee, Halter & Griswold LLP

(57) ABSTRACT

The present invention is directed to methods, reagents, kits and compositions for detecting microRNA (miRNA) precursors in a biological sample. The methods uses gene-specific primers and reverse transcriptase to convert the primary miRNA precursors (pri-miRNA) and pre-miRNA precursors (pre-miRNAs) to cDNA. The method also uses amplification reactions using gene specific forward and reverse primers that are targeted to the hairpin sequence of pri- and pre-microRNA precursors to detect the expression levels of both the pri- and the pre-microRNAs.

28 Claims, 18 Drawing Sheets

OTHER PUBLICATIONS

Lagos-Quintana, et al., "Identification of tissue-specific microRNAs from mouse", Curr Biol, 2002, 12 (9), pp. 735-739.

Lagos-Quintana, et al., "New microRNAs from mouse and human", RNA, 2003, 9 (2), pp. 175-179.

Lau et al., "An abundant class of tiny RNAs with probable regulatory roles in Caenorhabditis elegans", Science, vol. 294, pp. 858-862, Oct. 26, 2001.

Lee et al., "The C elegans heterochronic gene lin-4 encodes small RNAs with antisense complementarity to lin-14", Cell 1993, 75 (5), pp. 843-854.

Lee et al., "An extensive class of small RNAs in Caenorhabditis elegans", Science, 2001, 294 (5543), pp. 862-864.

Lee et al., "Expression of small interfering RNAs targeted against HIV-1 rev transcripts in human cells", Nat Biotechnol, 2002, 20 (5), pp. 500-505.

Lee et al., "MicroRNA maturation: stepwise processing and sebcullular localization", Embo J, 2002, 21 (17), pp. 4663-4670.

Lee et al., "The nuclear RNase III Drosha initiates microRNA processing", Nature, 425 (6956), pp. 415-419, 2003.

Lee et al., "Expression profiling identifies microRNA signature in pancreatic cancer", Int. J. Cancer, 120, pp. 1046-1054 (2006).

Lee et al., "Systematic evaluation of microRNA processing patterns in tissues, cell lines, and tumors", RNA, 14: 1-8, 2008.

Liu et al., "An oligonucleotide microchip for genome-wide microRNA profiling in human and mouse tissues", PNAS, vol. 101, No. 26, pp. 9740-9744, Jun. 29, 2004.

Lu et al., "MicroRNA expression profiles classify human cancers", Nature, Letters, vol. 435, pp. 834-838, Jun. 9, 2005.

Livak et al., Analysis of relative gene expression data using real-time quantitative PCR and the 2(-Delta Delta C(T)) Method, Methods, 2001, 25 (4): pp. 402-408.

Michael et al., "Reduced accumulation of specifc microRNAs in colorectal neoplasia", Mol Cancer Res, 2003, 1 (12), pp. 882-891.

Healthcare Mergers, Acquisitions & Ventures Week, Ohio State University, "High-throughput method developed for microRNA expression monitoring", May 17, 2004, 1 pg.

Ririe, et al., "Product differentiation by analysis of DNA melting curves during the polymerase chain reaction", Anal Biochem, 245-154-160, 1997.

Schmittgen et al., "Effect of expermental treatment of housekeeping gene expession: validation by real time, quantitative RT-PCR", J Biochem Biophys Methods, 2000, 46 (1-2), pp. 69-81.

Schmittgen et al., "A high-throughput method to monitor the expression of microRNA precursors", Nucleic Acids Research, vol. 32, No. 4, 10 pgs., 2004.

Stoflet et al., "Genomic amplification with transcript sequencing", Science, vol. 239, Reports, pp. 491-494, Jan. 29, 1988.

Takamizawa et al., "Reduced expression of the let-7 MicroRNAs in human lung cancers in association with shortened postoperative survival", Cancer Research, 64, pp. 3753-3756, Jun. 1, 2004.

Xu et al., "The drosophila microRNA Mir-14 suppresses cell death and is required for normal fat metabolism", Curr Biol, 2003, 13 (9), pp. 790-795.

Zeng et al., "Sequence requirements for micro RNA processing and function in human cells", RNA, 2003, 9 (1), pp. 112-123.

* cited by examiner

| Intraassay variation from replicate RNA isolations. Total RNA was isolated from triplicate samples of HeLa, HCT-116 and HL-60 cells. Each sample of RNA was independently reverse transcribed to cDNA and the expression of miR-18, -107 and -29 (relative to U6 RNA) was determined using real-time PCR. The mean, standard deviation and coefficient of variation from the replicate RNA isolations/reverse transcriptions are shown. | | | |
|---|---|---|---|
| Cell Line | Relative gene expression ($\times 10^6$) Mean $\pm$ SD, CV (%) | | |
|  | miR-18 | miR-107 | miR-29 |
| HeLa | 40.6 $\pm$ 1.12 (2.77 %) | 21.9 $\pm$ 0.462 (2.11 %) | 1.28 $\pm$ 0.145 (11.3 %) |
| HCT-116 | 24.2 $\pm$ 2.02 (8.32 %) | 20.2 $\pm$ 0.869 (4.30 %) | 6.40 $\pm$ 0.349 (5.45 %) |
| HL-60 | 55.9 $\pm$ 3.96 (7.07 %) | 22.3 $\pm$ 0.391 (1.75 %) | 0.370 $\pm$ 0.128 (34.5%) |

Figure 10

| Efficiency of amplification for miRNA genes and U6 RNA. | | | |
|---|---|---|---|
| Gene | Tm primers (° C) (Forward/Reverse) | PCR Efficiency | $r^2$ |
| miR-147 | 53/53 | 1.89 | 0.9996 |
| miR-29 | 49/51 | 1.93 | 0.9956 |
| miR-107 | 55/56 | 1.90 | 0.9990 |
| miR-27a | 56/56 | 1.96 | 0.9978 |
| miR-124a-2 | 58/58 | 1.93 | 0.9985 |
| miR-219 | 59/59 | 1.97 | 0.9984 |
| U6 | 59/59 | 1.94 | 0.9997 |

Figure 11

A hsa-let-7 Family, precursor miRNAs

```
hsa-let-7b    -----CGGGGUGAGGUAGUAGGUUGUGUGGUUUC-AGGGCAGUGA-UGUUGCCCC---UCGGAAGAUAACUAUACAACCUACUGCCUUCCCUG-----
hsa-let-7f-1  ----UCAGAGUGAGGUAGUAGAUUGUAUAGUUGU-GGGGUAGUGA-UUUUACCCUG-UUCAGGAGAUAACUAUACAAUCUAUUGCCUUCCCUGA----
hsa-let-7f-2  ---UGUGGGAUGAGGUAGUAGAUUGUAUAGUUUU-AGGG-------UCAUACCC-CAUCUUGGAGAUAACUAUACAGUCUACUGUCUUUCCCACG---
hsa-let-7a-1  -----UGGGAUGAGGUAGUAGGUUGUAUAGUUUU-AGGG-------UCACACCCACCACUGGGAGAUAACUAUACAAUCUACUGUCUUUCCUA-----
hsa-let-7a-2  ------AGGUUGAGGUAGUAGGUUGUAUAGUUU--AGAA--------UUACAU---CAAGGGAGAUAACUGUACAGCCUCCUAGCUUUCCU------
hsa-let-7a-3  -------GGGUGAGGUAGUAGGUUGUAUAGUUUG-GGGC-------UCUGCCCU---GCUAUGGGAUAACUAUACAAUCUACUGUCUUUCCU------
hsa-let-7c    GCAUCCGGGUUGAGGUAGUAGGUUGUAUGGUUU--AGAG---------UUACAC---CCUGGGAGUUAACUGUACAACCUUCUAGCUUUCCUUGGAGC
hsa-let-7e    ---CCCGGGCUGAGGUAGGAGGUUGUAUAGUUG--AGGA---------GGACAC---CCAAGGAGAUCACUAUACGGCCUCCUAGCUUUCCCCCAGG--
hsa-let-7d    ---CCUAGGAAGAGGUAGUAGGUUGCAUAGUUUU-AGGCAGGGA-UUUUGCCC---ACAAGGAGGUAACUAUACGACCUGCUGCCUUUCUUAGG---
hsa-let-7g    ------AGGCUGAGGUAGUAGUUUGUACAGUUUG-AGGGUCAUG-AUACCACCCGGUACAGGAGAUAACUGUACAGGCCACUGCCUUGCCA------
hsa-let-7i    -----CUGGCUGAGGUAGUAGUUUGUGCUGUUGGUCGGGUUGUGA-CAUUGCCC---GCUGUGGAGAUAACUGCGCAAGCUACUGCCUUGCUA------
```

Mature miRNAs
```
hsa-let-7b  UGAGGUAGUAGGUUGUGUGGUU
hsa-let-7c  UGAGGUAGUAGGUUGUAUGGUU
hsa-let-7d  AGAGGUAGUAGGUUGCAUAGU-
hsa-let-7e  UGAGGUAGGAGGUUGUAUAGU-
hsa-let-7a  UGAGGUAGUAGGUUGUAUAGUU
hsa-let-7f  UGAGGUAGUAGAUUGUAUAGUU
hsa-let-7g  UGAGGUAGUAGUUUGUACAGU-
hsa-let-7i  UGAGGUAGUAGUUUGUGCU---
```

B

```
hsa-let-7d  ---CCUAGGAAGAGGUAGUAGGUUGCAUAGUUUU-AGGCAGGGA-UUUUGCCC---ACAAGGAGGUAACUAUACGACCUGCUGCCUUUCUUAGG---
hsa-let-7g  ------AGGCUGAGGUAGUAGUUUGUACAGUUUG-AGGGUCUAUG-AUACCACCCGGUACAGGAGAUAACUGUACAGGCCACUCGGUUGCCA------
```

| PCR Primers used to amplify the human miRNAs precursors. p, primers to miRNA primary precursor sequence. All others primers hybridize to hairpin present in both the primary precursor (pri-miRNA) and pre- miRNA precursor (pre-miRNA). | | | | |
|---|---|---|---|---|
| Gene | Amplifies mouse sequence | Forward primer (5' → 3') | Reverse primer (5' → 3') | Tm primers (Forward/ Reverse) °C |
| U 6 | Yes | CTCGCTTCGGCAGCACA | AACGCTTCACGAATTTGCGT | 59/59 |
| miR-001-1 | Yes | AAACATACTTCTTTATATGCCCA | TACATACTTCTTTACATTCCATAGC | 52/51 |
| miR-001-2 | Yes | ACATACTTCTTTATGTACCCATATG | TACATACTTCTTTACATTCCATAGC | 50/51 |
| miR-007-1 | Yes | TGGAAGACTAGTGATTTTGTTGT | AGACTGTGATTTGTTGTCGATT | 52/53 |
| miR-007-2 | Yes | TGGAAGACTAGTGATTTTGTTGT | AGACTGGGATTTGTTGTTGAG | 52/53 |
| miR-007-3 | Yes | TGGAAGACTAGTGATTTTGTTGT | GGCTGTGACTTGTTGTCGTA | 52/53 |
| miR-009-1(p) | No | GGAGGCTGCGTGGAAGAG | CGTGAGGCCGGCTTTC | 58/57 |
| miR-009-2(p) | No | CTGGAGTCTGGCAAGAGGA | AGTCTTTCATTCTCACACGCTC | 55/55 |
| miR-009-3(p) | No | CAGCGGCACTGGCTAAG | GCTCGCACGCAGAAGTT | 55/55 |
| miR-010a,b | Yes | TACCCTGTAGATCCGAATTTGTG | ATTCCCCTAGATACGAATTTGTGA | 57/57 |
| miR-015a | Yes | CAGCACATAATGGTTTGTGGA | GCAGCACAATATGGCCTG | 56/55 |
| miR-015b | Yes | AGCACATCATGGTTTACATGC | CTAGAGCAGCAAATAATGATTCG | 55/55 |
| miR-016-1 | Yes | GCAGCACGTAAATATTGGCGT | CAGCAGCACAGTTAATACTGGAGA | 59/57 |
| miR-016-2 | Yes | GCACGTAAATATTGGCGTAGT | AAGCAGCACAGTAATATTGGTG | 54/54 |
| miR-017(p) | No | GCAGGAAAAAGAGAACATCACC | TGGCTTCCCGAGGCAG | 58/58 |
| miR-018 | Yes | TAAGGTGCATCTAGTGCAGATAG | GAAGGAGCACTTAGGGCAGT | 53/55 |
| miR-019a(p) | No | CCAATAATTCAAGCCAAGCA | CAGGCAGATTCTACATCGACA | 55/55 |
| miR-019b-1(p) | No | CCTGTCGCCCAATCAAA | CAACCTGTGTAGAAAGGGGTT | 55/55 |
| miR-019b-2(p) | No | GGCACTTCCAGTACTCTTGGA | GTGTGTTCACACAGACGTAGGA | 56/55 |
| miR-020 | Yes | GCACTAAAGTGCTTATAGTGCAG | GTACTTTAAGTGCTCATAATGCA | 53/51 |
| miR-021 | Yes | GCTTATCAGACTGATGTTGACTG | CAGCCCATCGACTGGTG | 53/55 |
| miR-022(p) | No | AGCAACATGCCCTGCTC | TCTGTCACCTTCCAGATGATG | 54/55 |
| miR-023a | Yes | CTGGGGTTCCTGGGGAT | TGGTAATCCCTGGCAATGTG | 57/58 |
| miR-023b(p) | No | AAGCCCAGTGTGTGCAGAC | ACCACGGTTTCTGGAGGA | 56/55 |
| miR-024-1,2 | Yes | CTCCCGTGCCTACTGAGCT | CCCTGTTCCTGCTGAACTGAG | 57/59 |
| miR-025 | Yes | TGAGAGGCGGAGACTTGG | TCAGACCGAGACAAGTGCAA | 56/57 |
| miR-026a-1,2 | Yes | TTCAAGTAATCCAGGATAGGCTGT | TGCAAGTAACCAAGAATAGGCC | 57/57 |
| miR-026b | Yes | TTCAAGTAATCCAGGATAGGCTGT | CAAGTAATGGAGAACAGGCTG | 57/54 |
| miR-027a,b | Yes | GCAGGGCTTAGCTGCTTG | GGCGGAACTTAGCCACTGT | 56/56 |
| miR-028 | Yes | GGAGCTCACAGTCTATTGAGTTACC | CCTCCAGGAGCTCACAATCT | 56/56 |

Figure 15

| | | | | |
|---|---|---|---|---|
| miR-029a,c | Yes | ATGACTGATTTCTTTTGGTG | ATAACCGATTTCAGATGGTG | 49/51 |
| miR-029b-1,2 | No | TGGTTTCATATGGTGGTTTA | ATAACCGATTTCAGATGGTG | 50/51 |
| miR-030a,e | Yes | GTAAACATCCTCGACTGGAAGCT | GCTGCAAACATCCGACTGAA | 58/58 |
| miR-030a(p) | Yes | AGGTTAACCCAACAGAAGGCT | CCTTGAAGTCCGAGGCAG | 56/55 |
| miR-030e(p) | Yes | CCTCACTGCGTCTCCGT | CCTGTGGGCACAAACCT | 54/54 |
| miR-030b | No | CATGTAAACATCCTACACTCAGCT | ATCCACCTCCCAGCCAAT | 54/56 |
| miR-030b(p) | Yes | GTGAATGCTGTGCCTGTTC | GCCTCTGTATACTATTCTTGCCA | 54/54 |
| miR-030c-1,2 | Yes | TGTGTAAACATCCTACACTCTCAG | GAGTAAACAACCCTCTCCCA | 53/53 |
| miR-030c-1(p) | No | CAGTGGTCAGGGGCTGAT | GGAGTGGAGACTGTTCCTTCT | 55/54 |
| miR-030c-2(p) | No | GACTGCCAACCCCATCCTA | CCTCAGAAACAAACACGGGA | 57/57 |
| miR-030d | Yes | GTTGTTGTAAACATCCCCGAC | GCAGCAAACATCTGACTGAAAG | 56/56 |
| miR-030d(p) | No | GCTGAAGATGATGACTGGCA | CTCCACTCCGGGACAGAA | 56/56 |
| miR-031(p) | Yes | TGAGTGTGTTTTCCCTCCCT | GCCATGGCTGCTGTCAG | 56/56 |
| miR-032 | Yes | GCACATTACTAAGTTGCATGTTG | TATCACACACACTAAATTGCATTG | 54/54 |
| miR-033 | Yes | TGTGGTGCATTGTAGTTGCA | CTGTGATGCACTGTGGAAAC | 56/54 |
| miR-034a | Yes | TGGCAGTGTCTTAGCTGGTTG | GGCAGTATACTTGCTGATTGCTT | 58/57 |
| miR-034b | No | GCAGTGTCATTAGCTGATTGTAC | GATGGCAGTGGAGTTAGTGAT | 53/53 |
| miR-034c | No | GCAGTGTAGTTAGCTGATTGCTAA | CCTGGCCGTGTGGTTAGT | 55/56 |
| miR-092-1 | No | TCTACACAGGTTGGGATCGG | CGGGACAAGTGCAATACCATA | 57/57 |
| miR-092-2(p) | No | ATGCGTATCTCCAGCACTCA | CCACCCGACAACAGCAA | 55/56 |
| miR-093 | Yes | AAGTGCTGTTCGTGCAGGT | CTCGGGAAGTGCTAGCTCA | 55/55 |
| miR-095 | No | GGCACTCAATAAATGTCTGTTGA | TGCTCAATAAATACCCGTTGA | 56/55 |
| miR-096(p) | No | AGAGAGCCCGCACCAGT | CTTGAGGAGGAGCAGGCT | 55/54 |
| miR-098 | Yes | GGTAGTAAGTTGTATTGTTGTGGG | TATAGTTATCTTCTAATTGGGGCC | 54/54 |
| miR-099a | Yes | TAAACCCGTAGATCCGATCTTG | CCACAGACACGAGCTTGTG | 57/55 |
| miR-099b | No | CCCACCCGTAGAACCGAC | CCACAGACACGAGCTTGTGT | 57/56 |
| miR-100 | Yes | AACCCGTAGATCCGAACTTG | TACCTATAGATACAAGCTTGTGCG | 55/55 |
| miR-101-1 | Yes | GCCCTGGCTCAGTTATCACA | GCCATCCTTCAGTTATCACAGTA | 57/55 |
| miR-101-2 | Yes | TTTTCGGTTATCATGGTACC | CCTTCAGTTATCACAGTACTGTACC | 51/53 |
| miR-103-1,2 | Yes | GCTTCTTTACAGTGCTGCCT | TTCATAGCCCTGTACAATGCT | 54/54 |
| miR-105-1,2 | Yes | CAAATGCTCAGACTCCTGTGGT | GCACATGCTCAAACATCCGT | 58/58 |
| miR-106a(p) | No | CTGCATGGATCTGTGAGGAC | AGCAGCTCAAAAGCATCAAC | 55/54 |
| miR-106b | Yes | TAAAGTGCTGACAGTGCAGATAGTG | CAAGTACCCACAGTGCGGT | 57/56 |
| miR-107 | Yes | CAGCTTCTTTACAGTGTTGCCT | GATAGCCCTGTACAATGCTGC | 55/56 |
| miR-108 | Yes | GGATTTTTAGGGGCATTATGAC | GAGGGACTTTCAGGGGCA | 58/58 |
| miR-122a | No | GGAGTGTGACAATGGTGTTTG | TTTAGTGTGATAATGGCGTTTG | 55/54 |
| miR-124a-1,2,3 | Yes | TCCGTGTTCACAGCGGAC | CATTCACCGCGTGCCTTA | 58/58 |

Figure 15 continued

| | | | | |
|---|---|---|---|---|
| miR-125a | Yes | GTCCCTGAGACCCTTTAACC | AACCTCACCTGTGACCCTG | 54/54 |
| miR-125b-1 | Yes | GTCCCTGAGACCCTAACTTG | AGCCTAACCCGTGGATTT | 52/53 |
| miR-125b-2 | Yes | GTCCCTGAGACCCTAACTTG | AAGAGCCTGACTTGTGATGT | 52/51 |
| miR-126 | Yes | TATTACTTTTGGTACGCGCTG | GCGCATTATTACTCACGGTAC | 55/54 |
| miR-127 | Yes | AGCCTGCTGAAGCTCAGAGG | GCCAAGCTCAGACGGATCC | 59/59 |
| miR-128a | Yes | TGGATTCGGGGCCGTAG | AAAGAGACCGGTTCACTGTGAG | 59/57 |
| miR-128b | Yes | GGAAGGGGGGCCGATA | AAAGAGACCGGTTCACTGTGAG | 58/57 |
| miR-129-2 | Yes | CTTTTTGCGGTCTGGGCT | GCTTTTTGGGGTAAGGGCT | 57/57 |
| miR-130a(p) | No | TGAGTGGGCCAGGGAC | GCAATGCTGAGGAGGCA | 54/55 |
| miR-130b | No | CCTGTTGCACTACTATAGGCCG | TGCCCTTTTAACATTGCACTG | 58/57 |
| miR-132 | Yes | AACCGTGGCTTTCGATTGTTA | CGACCATGGCTGTAGACTGTTAC | 58/57 |
| miR-133a-1,2 | Yes | GAGCTGGTAAAATGGAACCAAA | ACAGCTGGTTGAAGGGGAC | 57/56 |
| miR-133b | Yes | CTGGTCAAACGGAACCAAG | ACAGCTGGTTGAAGGGGAC | 55/56 |
| miR-134 | Yes | GTGACTGGTTGACCAGAGGG | GGTGACTAGGTGGCCCACA | 57/58 |
| miR-135a-1,2 | Yes | CTATGGCTTTTTATTCCTATGTGA | CACGGCTCCAATCCCTA | 54/54 |
| miR-135b(p) | No | GCTTCTCGCTTCCCTATGA | TCCGAACCTGGTCCCA | 54/55 |
| miR-136 | Yes | GGACTCCATTTGTTTTGATGATG | AGACTCATTTGAGACGATGATGG | 57/57 |
| miR-137 | Yes | GTGACGGGTATTCTTGGGT | GACTACGCGTATTCTTAAGCAA | 53/53 |
| miR-138-1,2 | Yes | CAGCTGGTGTTGTGAATCAG | ACCCTGGTGTCGTGAAATAG | 54/54 |
| miR-139 | Yes | TTCTACAGTGCACGTGTCTCCA | TACTCCAACAGGGCCGC | 58/57 |
| miR-140 | Yes | CAGTGGTTTTACCCTATGGTAGG | CGTGGTTCTACCCTGTGGTAG | 56/56 |
| miR-141 | Yes | GTCCATCTTCCAGTACAGTGTTG | AGCCATCTTTACCAGACAGTGT | 55/54 |
| miR-142(p) | No | TTGGAGCAGGAGTCAGGA | CGCCGAGGAAGATGGT | 54/54 |
| miR-143 | Yes | TGAGGTGCAGTGCTGCATC | GCTACAGTGCTTCATCTCAGACTC | 58/56 |
| miR-144 | Yes | GCTGGGATATCATCATATACTG | CGGACTAGTACATCATCTATACTG | 50/49 |
| miR-145(p) | No | GGATGCAGAAGAGAACTCCA | CCTCATCCTGTGAGCCAG | 54/53 |
| miR-146 | Yes | TTGAGAACTGAATTCCATGG | GCTGAAGAACTGAATTTCAGAG | 52/52 |
| miR-147 | No | CTAAAGACAACATTTCTGCACAC | ATCTAGCAGAAGCATTTCCAC | 53/53 |
| miR-148a(p) | Yes | GAGGAAGACAGCACGTTTGGT | AAAGGCGCAGCGACGT | 58/58 |
| miR-148b(p) | Yes | TCTGTCTAAGTCACCCAATCTC | TCTATTCTTCCCTCCCACTC | 52/52 |
| miR-149 | Yes | CTGGCTCCGTGTCTTCACT | AGCACAGCCCCCGTCC | 57/59 |
| miR-150 | Yes | GTCTCCCAACCCTTGTACCAG | TGTCCCCCAGGCCTGTAC | 57/58 |
| miR-151 | Yes | CTCGAGGAGCTCACAGTCTAG | GTCCTCAAGGAGCTTCAGTC | 53/53 |
| miR-152 | Yes | GCCCAGGTTCTGTGATACACT | CCCAAGTTCTGTCATGCAC | 55/53 |
| miR-153-1,2 | Yes | CATTTTTGTGATCTGCAGCTAGT | TCACTTTTGTGACTATGCAACTG | 55/54 |
| miR-154 | Yes | TAGGTTATCCGTGTTGCCTT | AATAGGTCAACCGTGTATGATTC | 54/54 |
| miR-155 | No | GTTAATGCTAATCGTGATAGGG | GCTAATATGTAGGAGTCAGTTGGA | 52/53 |
| miR-181a,c | Yes | AACATTCAACGCTGTCGGT | CAGTCAACGGTCAGTGGTTT | 55/55 |
| miR-181b-1,2 | Yes | AACATTCAACGCTGTCGGT | TTGCATTCATTGTTCAGTGAG | 55/53 |

Figure 15 continued

| | | | | |
|---|---|---|---|---|
| miR-182 | Yes | TTTGGCAATGGTAGAACTCAC | GTTGGCAAGTCTAGAACCACC | 54/55 |
| miR-183 | Yes | GTATGGCACTGGTAGAATTCAC | TATGGCCCTTCGGTAATTC | 53/54 |
| miR-184 | Yes | CTTATCACTTTTCCAGCCCA | CCTTATCAGTTCTCCGTCCA | 54/54 |
| miR-185 | No | GGAGAGAAAGGCAGTTCCTG | GGACCAGAGGAAAGCCAG | 55/54 |
| miR-186(p) | No | CACCCATCATATTCTTCCCA | GACATTCACATGCTTCAGGTAG | 54/54 |
| miR-187 | Yes | CTCGGGCTACAACACAGGA | GCTGCAACACAAGACACGA | 56/55 |
| miR-188(p) | No | CCATATGTCGTGCCAAGAGA | CACATGCACAAGAGAGCAAG | 56/54 |
| miR-190 | Yes | GTGATATGTTTGATATATTAGGTTG | GGAATATGTTTGATATATAGTTGG | 49/49 |
| miR-191 | No | GCAACGGAATCCCAAAAG | GACGAAATCCAAGCGCA | 55/55 |
| miR-192 | No | CTGACCTATGAATTGACAGCC | TGACCTATGGAATTGGCAG | 54/53 |
| miR-193 | Yes | GTCTTTGCGGGCGAGAT | AACTGGGACTTTGTAGGCCA | 56/56 |
| miR-194-1,2 | No | TGTAACAGCAACTCCATGTG | TAACAGCATCTCCACTGGAA | 52/53 |
| miR-195(p) | No | GGAGTCTTTGTTGCCCACA | GGCTCAGCCCCTCCTC | 56/55 |
| miR-196a-1 | No | TAGGTAGTTTCATGTTGTTGGG | ATCGGGTGGTTTAATGTTG | 53/52 |
| miR-196a-2 | Yes | TAGGTAGTTTCATGTTGTTGGG | CAGTTTCTTGTTGCCGAGTT | 53/54 |
| miR-196b | Yes | TAGGTAGTTTCATGTTGTTGGG | AGGCAGTGTCGTGCTGT | 53/52 |
| miR-197 | Yes | CTGTGCCGGGTAGAGAGG | ATGCTGGGTGGAGAAGGT | 55/54 |
| miR-198 | No | GGTCCAGAGGGGAGATA | TTTATTCTATAGAGAAGAAGGAAA | 49/48 |
| miR-199a-1(p) | Yes | GTGGTGGTTTCCTTGGCT | GGTGGTGGAAAATGACACTC | 54/54 |
| miR-199a-2(p) | No | GGAGGCTTTTCCTGAGGAC | CCCTAGTGTGCAAAACCTGT | 54/55 |
| miR-199b(p) | No | CACCGGATGGACAGACA | CGGTCCAGCTCTCCAGT | 53/53 |
| miR-200a(p) | No | TTCCACAGCAGCCCCTG | GATGTGCCTCGGTGGTGT | 58/56 |
| miR-200b | Yes | CATCTTACTGGGCAGCATTG | GTCATCATTACCAGGCAGTATTAG | 55/54 |
| miR-200c | Yes | CTCGTCTTACCCAGCAGTGT | GTCATCATTACCAGGCAGTATTAG | 54/54 |
| miR-203 | Yes | TCCAGTGGTTCTTAACAGTTCA | GGTCTAGTGGTCCTAAACATTTC | 54/53 |
| miR-204 | Yes | CCCTTTGTCATCCTATGCCT | GTCCCTTTGCCTTCCCA | 55/55 |
| miR-205 | Yes | CCTTCATTCCACCGGAGT | GAACTTCACTCCACTGAAATCTG | 54/54 |
| miR-206 | Yes | ACATGCTTCTTTATATCCCCA | AAACCACACACTTCCTTACATTC | 53/54 |
| miR-208 | Yes | AGCTTTTGGCCCGGGTT | CCAACAAGCTTTTTGCTCGTC | 59/59 |
| miR-210 | Yes | CCTGCCCACCGCACACT | AGCCGCTGTCACACGCA | 60/60 |
| miR-211 | Yes | CCTTTGTCATCCTTCGCCT | CCCCTTTGCTGTCCCTG | 56/56 |
| miR-212 | Yes | CACCTTGGCTCTAGACTGCTT | GCCGTGACTGGAGACTGTTA | 55/55 |
| miR-213 | Yes | GAACATTCAACGCTGTCGGT | GTACAATCAACGGTCGATGG | 57/56 |
| miR-214 | Yes | TCTGCCTGTCTACACTTGCTG | TGACTGCCTGTCTGTGCCT | 55/56 |
| miR-215 | No | ATGACCTATGAATTGACAGACAAT | TTGGCCTAAAGAAATGACAGAC | 53/55 |
| miR-216 | Yes | TGGCTTAATCTCAGCTGGCA | TGAGGGCTAGGAAATTGCTCT | 58/58 |
| miR-217 | Yes | GATACTGCATCAGGAACTGATTG | GGCAATGCATTAGGAACTGAT | 55/55 |
| miR-218-1,2 | Yes | GTGCTTGATCTAACCATGTGGT | GTGCTTGACGGAACCATGTT | 55/57 |
| miR-219-1,2 | Yes | TCCTGATTGTCCAAACGCAA | GGGACGTCCAGACTCAACTCTC | 59/59 |
| miR-220 | Yes | CCACACCGTATCTGACACTTT | CAGACCGCATCATGAACAC | 54/54 |

Figure 15 continued

| miR-221 | Yes | CCTGGCATACAATGTAGATTTCTG | AAACCCAGCAGACAATGTAGCT | 57/57 |
|---|---|---|---|---|
| miR-222(p) | No | CCCCAGAAGGCAAAGGAT | CTCTCTCAGGACACTGAAGCAG | 56/56 |
| miR-223 | Yes | CCGTGTATTTGACAAGCTGAGT | TGGGGTATTTGACAAACTGACA | 56/57 |
| miR-224 | Yes | GGCTTTCAAGTCACTAGTGGTTC | CTTTGTAGTCACTAGGGCACCA | 56/56 |
| miR-296 | Yes | CCCCCCCTCAATCCTGT | GGAGAGCCTCCACCCAAC | 57/57 |
| miR-299(p) | No | ACCACCATCGTGCGGTA | GTTTGGATGGCTGGGCT | 55/55 |
| miR-301 | Yes | GCTCTGACTTTATTGCACTACTG | GCTTTGACAATACTATTGCACTG | 53/53 |
| miR-302 | Yes | CCACTTAAACGTGGATGTACTTG | TCACCAAAACATGGAAGCAC | 55/56 |
| miR-302b | Yes | CAACTTTAACATGGAAGTGCTTT | CCTACTAAAACATGGAAGCACTTAC | 54/55 |
| miR-302c | No | GCTTTAACATGGGGGTACCT | TCACCAAAACATGGAAGCAC | 54/56 |
| miR-302d | Yes | TCTACTTTAACATGGAGGCACTT | TCACCAAAACATGGAAGCAC | 54/56 |
| miR-320 | Yes | CGCCTTCTCTTCCCGGT | TTCGCCCTCTCAACCCA | 57/57 |
| miR-321 | Yes | CTAAGCCAGGGATTGTGGG | CTTTACCCCGGGTGGG | 57/56 |
| miR-323 | Yes | AGAGGTGGTCCGTGGCG | GAGGTCGACCGTGTAATGTGC | 59/59 |
| miR-324(p) | Yes | CATTGCTGTCTCTCTTCGCA | TGGGGCTTTCTTCCCAG | 56/56 |
| miR-325 | Yes | CCTAGTAGGTGTCCAGTAAGTGT | GATAGGAGGTCCTCAATAAACA | 51/52 |
| miR-326(p) | No | CGGGACTCCCATCAAGAA | CTGGAAGCTGAAGCTGCAT | 55/55 |
| miR-328 | Yes | GAGGGGCTCAGGGAGAAAG | GGACGGAAGGGCAGAGA | 57/56 |
| miR-330 | Yes | CTGGGCCTGTGTCTTAGGCT | TGCAGGCCGTGTGCTTT | 58/58 |
| miR-331(p) | No | GAGCTGAAAGCACTCCCAA | CACACTCTTGATGTTCCAGGA | 55/55 |
| miR-335 | Yes | GTCAAGAGCAATAACGAAAAATG | GAGGTCAGGAGCAATAATGAA | 55/53 |
| miR-337 | No | ACGGCTTCATACAGGAGTTG | GGCATCATATAGGAGCTGGA | 54/54 |
| miR-338 | Yes | CCAACAATATCCTGGTGCTGAG | CAACAAAATCACTGATGCTGGA | 58/57 |
| miR-339 | Yes | TCCCTGTCCTCCAGGAGCT | TCTGTCGTCGAGGCGCT | 58/58 |
| miR-340 | Yes | ATAAAGCAATGAGACTGATTGTC | GGCTATAAAGTAACTGAGACGGA | 52/54 |
| miR-342 | Yes | GTGCTATCTGTGATTGAGGGA | CGGGTGCGATTTCTGTG | 54/55 |
| miR-345 | No | CTGACTCCTAGTCCAGGGCT | CTCCAGACCCCTCGTTCA | 55/56 |
| miR-346 | No | GCATGCCTGCCTCTCTGTTG | TGCCCAGGCAGCTGCA | 61/61 |
| miR-361 | Yes | CTTATCAGAATCTCCAGGGGTAC | GCAAATCAGAATCACACCTG | 55/53 |
| miR-367 | Yes | CTGTTGCTAATATGCAACTCTG | CACCATTGCTAAAGTGCAAT | 52/53 |
| miR-368 | Yes | GGTGGATATTCCTTCTATGTTTATG | AACGTGGAATTTCCTCTATGTT | 54/53 |
| miR-369 | No | GGAGATCGACCGTGTTATATTC | GAAAAGATCAACCATGTATTATTCG | 54/55 |
| miR-370 | Yes | GGTCACGTCTCTGCAGTTACA | ACCAGGTTCCACCCCAG | 55/55 |
| miR-371 | Yes | TCAAACTGTGGGGGCACTT | ACACTCAAAAGATGGCGGC | 58/57 |
| miR-372 | Yes | GCCTCAAATGTGGAGCACTATT | TCAAATGTCGCAGCACTTTC | 57/56 |
| miR-373 | No | CTCAAAATGGGGGCGCTT | CACCCCAAAATCGAAGCACT | 60/59 |
| miR-374(p) | No | GCCCTCAAGGAGCTCACAGT | CACCCCCTGGGAAGAAATTT | 58/59 |
| miR-375 | Yes | ACGAGCCCCTCGCACA | CCTCACGCGAGCCGAAC | 58/60 |
| miR-376a | Yes | GGTAGATTCTCCTTCTATGAGTAC | ACGTGGATTTTCCTCTATG | 49/49 |

Figure 15 continued

| miR-377 | Yes | GAGCAGAGGTTGCCCTTG | ACAAAAGTTGCCTTTGTGTGA | 55/55 |
|---|---|---|---|---|
| miR-378 | Yes | CTCCTGACTCCAGGTCCTGT | GCCTTCTGACTCCAAGTCCA | 55/56 |
| miR-379 | Yes | AGAGATGGTAGACTATGGAACGT | GTGGACCATGTTACATAGGTCAG | 53/55 |
| miR-380 | Yes | GATGGTTGACCATAGAACATG | GATGTGGACCATATTACATACGA | 52/53 |
| miR-381 | Yes | AGCGAGGTTGCCCTTTG | ACAGAGAGCTTGCCCTTGTATA | 56/55 |
| miR-382 | Yes | GAAGTTGTTCGTGGTGGATTC | AAGTGTTGTCCGTGAATGATTC | 56/55 |
| miR-383 | Yes | CAGATCAGAAGGTGATTGTGGCT | TTCTGACCAGGCAGTGCTGT | 59/58 |
| miR-384 | No | CAATTCCTAGACAATATGTATAATG | GTCATTCCTAGAAATTGTTCATA | 49/50 |
| miR-422b | Yes | TCCTGACTCCAGGTCCTGT | GGCCTTCTGACTCCAAGTC | 54/53 |
| miR-423 | Yes | TGAGGGGCAGAGAGCGA | GAGGGGCCTCAGACCGA | 58/58 |
| miR-424 | Yes | AGCAGCAATTCATGTTTTGAAG | GCAGCGCCTCACGTTTT | 56/57 |
| miR-425 | Yes | ATGACACGATCACTCCCGTTG | GGGCGGACACGACATTC | 59/57 |
| let7a-1 | Yes | AGGTAGTAGGTTGTATAGTTTTAGG | TAGGAAAGACAGTAGATTGTATAGT | 49/48 |
| let7a-1(p)* | No | CCTGGATGTTCTCTTCACTG | GCCTGGATGCAGACTTTTCT | 60/60 |
| let7a-2 | Yes | GAGGTAGTAGGTTGTATAGTTTAGAA | AAAGCTAGGAGGCTGTACA | 49/49 |
| let7a-2(p)* | Yes | TTCCAGCCATTGTGACTGCA | CTCACCATGTTGTTTAGTGC | 60/58 |
| let7a-3 | Yes | GAGGTAGTAGGTTGTATAGTTTGG | GGAAAGACAGTAGATTGTATAGTTAT | 50/49 |
| let7a-3(p)* | No | ACCAAGACCGACTGCCCTTT | CTCTGTCCACCGCAGATATT | 62/60 |
| let7b | Yes | TGAGGTAGTAGGTTGTGTGGT | GGAAGGCAGTAGGTTGTATAG | 51/50 |
| let7b(p) | Yes | CCTCCCGCAGTGCAAG | CATGGGGTCGTGTCACTG | 56/55 |
| let7c | Yes | TTGAGGTAGTAGGTTGTATGGTT | GGAAAGCTAGAAGGTTGTACAG | 51/52 |
| let7c(p) | Yes | TTGGAGGAGCTGACTGAAGA | AAGAATTCCTCGACGGCTC | 55/56 |
| let7d | Yes | AGGTTGCATAGTTTTAGGGCA | AAGGCAGCAGGTCGTATAGT | 55/53 |
| let7d(p) | No | GCCAAGTAGAAGACCAGCAAG | CAAGGAAACAGGTTATCGGTG | 56/56 |
| let7e | Yes | GAGGTAGGAGGTTGTATAGTTGAG | GAAAGCTAGGAGGCCGTATAG | 52/54 |
| let7e(p) | No | CTGTCTGTCTGTCTGTC | AGAAAAGAGCCCGGCTCTT | 57/57 |
| let7f-1 | Yes | GATTGTATAGTTGTGGGGTAGTG | GGGAAGGCAATAGATTGTATAG | 52/51 |
| let7f-1(p)* | Yes | TGTACTTTCCATTCCAGAAG | TAATGCAGCAAGTCTACTCC | 56/58 |
| let7f-2 | Yes | GGTAGTAGATTGTATAGTTTTAGGG | GGGAAAGACAGTAGACTGTATAGT | 49/50 |
| let7f-2(p)* | Yes | TGAAGATGGACACTGGTGCT | CAGTCGGAGAAGAAGTGTAC | 60/60 |
| let7g | Yes | GTAGTAGTTTGTACAGTTTGAGGGT | GGCAGTGGCCTGTACAGT | 52/53 |
| let7g(p) | No | AGCGCTCCGTTTCCTTTT | CCCCACTTGGCAGCTG | 56/55 |
| let7i | Yes | TGTGCTGTTGGTCGGGT | GCAGTAGCTTGCGCAGTT | 55/54 |
| let7i(p) | Yes | CGAGGAAGGACGGAGGA | GCTGAGCATCACCAGCAC | 56/55 |

\* Primer sequence identical to that reported in Takamizawa, J., H. Konishi, K. Yanagisawa, S. Tomida, H. Osada, H. Endoh, T. Harano, Y. Yatabe, M. Nagino, Y. Nimura, T. Mitsudomi, and T. Takahashi, Reduced expression of the let-7 microRNAs in human lung cancers in association with shortened postoperative survival. Cancer Res, 2004. 64(11): p. 3753-6.

Figure 15 continued

SEQUENCE LISTING

<160> NUMBER OF SEQ ID NOS: 470

<210> SEQ ID NO 1
<211> LENGTH: 62
<212> TYPE: RNA
<213> ORGANISM: Homo sapiens

<400> SEQUENCE: 1
uaaggugcau cuagugcaga uagugaauga gauuagcauc uacugcccua agugcuccuu    60
cu                                                                  62

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 2
uaaggugcau cuagugcaga ua                                            22

<210> SEQ ID NO 3
<211> LENGTH: 83
<212> TYPE: RNA
<213> ORGANISM: Homo sapiens

<400> SEQUENCE: 3
cggggugagg uaguagguug uguggutuuca gggcagugau guugcccuc ggaagauaac    60 uauacaaccu acugccuucc cug                                           83

<210> SEQ ID NO 4

```
<211> LENGTH: 87
<212> TYPE: RNA
<213> ORGANISM: Homo sapiens

<400> SEQUENCE: 4
ucagagugag guaguagauu guauaguugu gggguaguga uuuuacccug uucaggagau        60
aacuauacaa ucuauugccu ucccuga                                           87

<210> SEQ ID NO 5
<211> LENGTH: 83
<212> TYPE: RNA
<213> ORGANISM: Homo sapiens

<400> SEQUENCE: 5
ugugggauga gguaguagau uguauaguuu uagggucaua ccccaucuug gagauaacua        60
uacagucuac ugucuuuccc acg                                               83

<210> SEQ ID NO 6
<211> LENGTH: 80
<212> TYPE: RNA
<213> ORGANISM: Homo sapiens

<400> SEQUENCE: 6
ugggaugagg uaguagguug uauaguuuua gggucacacc caccacuggg agauaacuau        60
acaaucuacu gucuuuccua                                                   80

<210> SEQ ID NO 7
<211> LENGTH: 72
<212> TYPE: RNA
<213> ORGANISM: Homo sapiens

<400> SEQUENCE: 7
agguugaggu aguagguugu auaguuuaga auuacaucaa gggagauaac uguacagccu        60
ccuagcuuuc cu                                                           72

<210> SEQ ID NO 8
<211> LENGTH: 74
<212> TYPE: RNA
<213> ORGANISM: Homo sapiens

<400> SEQUENCE: 8
gggugaggua guagguugua uaguuugggg cucugcccug cuugggaua acuauacaau         60 cuacugucuu uccu                                                         74

<210> SEQ ID NO 9
<211> LENGTH: 84
<212> TYPE: RNA
<213> ORGANISM: Homo sapiens

<400> SEQUENCE: 9
gcauccgggu ugagguagua gguuguaugg uuuagaguua cacccuggga guuaacugua        60
caaccuucua gcuuuccuug gagc                                              84

<210> SEQ ID NO 10
<211> LENGTH: 79
<212> TYPE: RNA
<213> ORGANISM: Homo sapiens

<400> SEQUENCE: 10
cccgggcuga gguaggaggu uguauaguug aggaggacac ccaaggagau cacuauacgg        60
```

-continued

| | |
|---|---|
| ccuccuagcu uuccccagg | 79 |

<210> SEQ ID NO 11
<211> LENGTH: 87
<212> TYPE: RNA
<213> ORGANISM: Homo sapiens

<400> SEQUENCE: 11

| | |
|---|---|
| ccuaggaaga gguaguaggu ugcauaguuu uagggcaggg auuuugccca caaggaggua | 60 |
| acuauacgac cugcugccuu ucuuagg | 87 |

<210> SEQ ID NO 12
<211> LENGTH: 84
<212> TYPE: RNA
<213> ORGANISM: Homo sapiens

<400> SEQUENCE: 12

| | |
|---|---|
| aggcugaggu aguaguuugu acaguuugag ggucuaugau accacccggu acaggagaua | 60 |
| acuguacagg ccacugccuu gcca | 84 |

<210> SEQ ID NO 13
<211> LENGTH: 84
<212> TYPE: RNA
<213> ORGANISM: Homo sapiens

<400> SEQUENCE: 13

| | |
|---|---|
| cuggcugagg uaguaguuug ugcuguuggu cggguuguga cauugcccgc uguggagaua | 60 |
| acugcgcaag cuacugccuu gcua | 84 |

<210> SEQ ID NO 14
<211> LENGTH: 22
<212> TYPE: RNA
<213> ORGANISM: Homo sapiens

<400> SEQUENCE: 14

| | |
|---|---|
| ugagguagua gguugugugg uu | 22 |

<210> SEQ ID NO 15
<211> LENGTH: 22
<212> TYPE: RNA
<213> ORGANISM: Homo sapiens

<400> SEQUENCE: 15

| | |
|---|---|
| ugagguagua gguuguaugg uu | 22 |

<210> SEQ ID NO 16
<211> LENGTH: 21
<212> TYPE: RNA
<213> ORGANISM: Homo sapiens

<400> SEQUENCE: 16

| | |
|---|---|
| agagguagua gguugcauag u | 21 |

<210> SEQ ID NO 17
<211> LENGTH: 21
<212> TYPE: RNA
<213> ORGANISM: Homo sapiens

<400> SEQUENCE: 17

| | |
|---|---|
| ugagguagga gguuguauag u | 21 |

<210> SEQ ID NO 18

```
<211> LENGTH: 22
<212> TYPE: RNA
<213> ORGANISM: Homo sapiens

<400> SEQUENCE: 18
ugagguagua gguuguauag uu                                          22

<210> SEQ ID NO 19
<211> LENGTH: 22
<212> TYPE: RNA
<213> ORGANISM: Homo sapiens

<400> SEQUENCE: 19
ugagguagua gauuguauag uu                                          22

<210> SEQ ID NO 20
<211> LENGTH: 21
<212> TYPE: RNA
<213> ORGANISM: Homo sapiens

<400> SEQUENCE: 20
ugagguagua guuuguacag u                                           21

<210> SEQ ID NO 21
<211> LENGTH: 19
<212> TYPE: RNA
<213> ORGANISM: Homo sapiens

<400> SEQUENCE: 21
ugagguagua guuugugcu                                              19

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctcgcttcgg cagcaca                                                17

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aacgcttcac gaatttgcgt                                             20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaacatactt ctttatatgc cca                                         23

<210> SEQ ID NO 25
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tacatacttc tttacattcc atagc                                              25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acatacttct ttatgtaccc atatg                                              25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tacatacttc tttacattcc atagc                                              25

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggaagacta gtgattttgt tgt                                                23

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agactgtgat tgttgtcga tt                                                  22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tggaagacta gtgattttgt tgt                                                23

<210> SEQ ID NO 31
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 31
agactgggat tgttgttga g                                              21

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tggaagacta gtgattttgt tgt                                           23

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggctgtgact tgttgtcgta                                               20

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggaggctgcg tggaagag                                                 18

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgtgaggccg gctttc                                                   16

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctggagtctg gcaagagga                                                19

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 37
agtctttcat tctcacacgc tc                                              22

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cagcggcact ggctaag                                                    17

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctcgcacgc agaagtt                                                    17

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
taccctgtag atccgaattt gtg                                             23

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
attcccctag atacgaattt gtga                                            24

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cagcacataa tggtttgtgg a                                               21

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 43
gcagcacaat atggcctg                                                    18

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agcacatcat ggtttacatg c                                                21

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ctagagcagc aaataatgat tcg                                              23

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcagcacgta aatattggcg t                                                21

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cagcagcaca gttaatactg gaga                                             24

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcacgtaaat attggcgtag t                                                21

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
```
aagcagcaca gtaatattgg tg					22

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcaggaaaaa agagaacatc acc					23

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tggcttcccg aggcag					16

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
taaggtgcat ctagtgcaga tag					23

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaaggagcac ttagggcagt					20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccaataattc aagccaagca					20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caggcagatt ctacatcgac a					21

```
<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cctgtcgccc aatcaaa                                                     17

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caacctgtgt agaaaggggt t                                                21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggcacttcca gtactcttgg a                                                21

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtgtgttcac acagacgtag ga                                               22

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcactaaagt gcttatagtg cag                                              23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtactttaag tgctcataat gca                                              23

<210> SEQ ID NO 62
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcttatcaga ctgatgttga ctg                                            23

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cagcccatcg actggtg                                                   17

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
agcaacatgc cctgctc                                                   17

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tctgtcacct tccagatgat g                                              21

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctggggttcc tggggat                                                   17

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tggtaatccc tggcaatgtg                                                20

<210> SEQ ID NO 68
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 68
aagcccagtg tgtgcagac                                                    19

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
accacggttt ctggagga                                                     18

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctcccgtgcc tactgagct                                                    19

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccctgttcct gctgaactga g                                                 21

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgagaggcgg agacttgg                                                     18

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tcagaccgag acaagtgcaa                                                   20

<210> SEQ ID NO 74
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 74
ttcaagtaat ccaggatagg ctgt                                              24

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgcaagtaac caagaatagg cc                                                22

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ttcaagtaat ccaggatagg ctgt                                              24

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caagtaatgg agaacaggct g                                                 21

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gcagggctta gctgcttg                                                     18

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggcggaactt agccactgt                                                    19

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 80
ggagctcaca gtctattgag ttacc                                          25

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cctccaggag ctcacaatct                                                20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
atgactgatt tcttttggtg                                                20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ataaccgatt tcagatggtg                                                20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tggtttcata tggtggttta                                                20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ataaccgatt tcagatggtg                                                20

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
```

```
gtaaacatcc tcgactggaa gct                                              23
```

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

```
gctgcaaaca tccgactgaa                                                  20
```

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88

```
aggttaaccc aacagaaggc t                                                21
```

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

```
ccttgaagtc cgaggcag                                                    18
```

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

```
cctcactgcg tctccgt                                                     17
```

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

```
cctgtgggca caaacct                                                     17
```

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
catgtaaaca tcctacactc agct                                             24
```

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
atccacctcc cagccaat                                                 18

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gtgaatgctg tgcctgttc                                                19

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gcctctgtat actattcttg cca                                           23

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
tgtgtaaaca tcctacactc tcag                                          24

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gagtaaacaa ccctctccca                                               20

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cagtggtcag gggctgat                                                 18

-continued

```
<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ggagtggaga ctgttccttc t                                                21

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gactgccaac cccatccta                                                   19

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cctcagaaac aaacacggga                                                  20

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gttgttgtaa acatccccga c                                                21

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcagcaaaca tctgactgaa ag                                               22

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gctgaagatg atgactggca                                                  20

<210> SEQ ID NO 105
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ctccactccg ggacagaa                                                 18

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tgagtgtgtt ttccctccct                                               20

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gccatggctg ctgtcag                                                  17

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gcacattact aagttgcatg ttg                                           23

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
tatcacacac actaaattgc attg                                          24

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tgtggtgcat tgtagttgca                                               20

<210> SEQ ID NO 111
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 111
ctgtgatgca ctgtggaaac                                              20

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tggcagtgtc ttagctggtt g                                            21

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggcagtatac ttgctgattg ctt                                          23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gcagtgtcat tagctgattg tac                                          23

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gatggcagtg gagttagtga t                                            21

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gcagtgtagt tagctgattg ctaa                                         24

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 117
cctggccgtg tggttagt                                         18

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tctacacagg ttgggatcgg                                       20

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cgggacaagt gcaataccat a                                     21

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
atgcgtatct ccagcactca                                       20

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ccacccgaca acagcaa                                          17

<210> SEQ ID NO 122
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
aagtgctgtt cgtgcaggt                                        19

<210> SEQ ID NO 123
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 123
ctcgggaagt gctagctca                                          19

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ggcactcaat aaatgtctgt tga                                     23

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tgctcaataa atacccgttg a                                       21

<210> SEQ ID NO 126
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
agagagcccg caccagt                                            17

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
cttgaggagg agcaggct                                           18

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
ggtagtaagt tgtattgttg tggg                                    24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
```

```
tatagttatc ttctaattgg ggcc                                              24
```

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130

```
taaacccgta gatccgatct tg                                                22
```

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131

```
ccacagacac gagcttgtg                                                    19
```

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132

```
cccacccgta gaaccgac                                                     18
```

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133

```
ccacagacac gagcttgtgt                                                   20
```

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134

```
aacccgtaga tccgaacttg                                                   20
```

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135

```
tacctataga tacaagcttg tgcg                                              24
```

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gccctggctc agttatcaca                                                20

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gccatccttc agttatcaca gta                                            23

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttttcggtta tcatggtacc                                                20

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ccttcagtta tcacagtact gtacc                                          25

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gcttctttac agtgctgcct                                                20

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ttcatagccc tgtacaatgc t                                              21

<210> SEQ ID NO 142

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
caaatgctca gactcctgtg gt                                              22

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gcacatgctc aaacatccgt                                                 20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ctgcatggat ctgtgaggac                                                 20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
agcagctcaa aagcatcaac                                                 20

<210> SEQ ID NO 146
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
taaagtgctg acagtgcaga tagtg                                           25

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
caagtaccca cagtgcggt                                                  19

<210> SEQ ID NO 148
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 148
cagcttcttt acagtgttgc ct                                              22

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gatagccctg tacaatgctg c                                               21

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ggatttttag gggcattatg ac                                              22

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gagggacttt caggggca                                                   18

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ggagtgtgac aatggtgttt g                                               21

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
tttagtgtga taatggcgtt tg                                              22

<210> SEQ ID NO 154
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 154
tccgtgttca cagcggac                                                   18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cattcaccgc gtgcctta                                                   18

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gtccctgaga ccctttaacc                                                 20

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
aacctcacct gtgaccctg                                                  19

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gtccctgaga ccctaacttg                                                 20

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
agcctaaccc gtggattt                                                   18

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 160
gtccctgaga ccctaacttg                                                  20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
aagagcctga cttgtgatgt                                                  20

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
tattactttt ggtacgcgct g                                                21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
gcgcattatt actcacggta c                                                21

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
agcctgctga agctcagagg                                                  20

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gccaagctca gacggatcc                                                   19

<210> SEQ ID NO 166
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tggattcggg gccgtag                                                     17

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
aaagagaccg gttcactgtg ag                                               22

<210> SEQ ID NO 168
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168 ggaaggggggg ccgata                                                     16

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
aaagagaccg gttcactgtg ag                                               22

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170 cttttttgcgg tctgggct                                                   18

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gctttttggg gtaagggct                                                   19

<210> SEQ ID NO 172
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tgagtgggcc agggac                                                      16

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 173
gcaatgctga ggaggca                                              17

<210> SEQ ID NO 174
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 174
cctgttgcac tactataggc cg                                        22

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 175 tgcccttta acattgcact g                                          21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 176
aaccgtggct ttcgattgtt a                                         21

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 177
cgaccatggc tgtagactgt tac                                       23

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 178
gagctggtaa aatggaacca aa                                        22

-continued

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
acagctggtt gaagggggac                                               19

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ctggtcaaac ggaaccaag                                                19

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
acagctggtt gaagggggac                                               19

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gtgactggtt gaccagaggg                                               20

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ggtgactagg tggcccaca                                                19

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ctatggcttt ttattcctat gtga                                          24

<210> SEQ ID NO 185
<211> LENGTH: 17

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cacggctcca atcccta                                                        17

<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
gcttctcgct tccctatga                                                      19

<210> SEQ ID NO 187
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
tccgaacctg gtccca                                                         16

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
ggactccatt tgttttgatg atg                                                 23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
agactcattt gagacgatga tgg                                                 23

<210> SEQ ID NO 190
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gtgacgggta ttcttgggt                                                      19

<210> SEQ ID NO 191
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 191
gactacgcgt attcttaagc aa                                              22

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
cagctggtgt tgtgaatcag                                                 20

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
accctggtgt cgtgaaatag                                                 20

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ttctacagtg cacgtgtctc ca                                              22

<210> SEQ ID NO 195
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
tactccaaca gggccgc                                                    17

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
cagtggtttt accctatggt agg                                             23

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                                    primer

<400> SEQUENCE: 197
cgtggttcta ccctgtggta g                                              21

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gtccatcttc cagtacagtg ttg                                            23

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
agccatcttt accagacagt gt                                             22

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ttggagcagg agtcagga                                                  18

<210> SEQ ID NO 201
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
cgccgaggaa gatggt                                                    16

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tgaggtgcag tgctgcatc                                                 19

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 203
gctacagtgc ttcatctcag actc                                            24

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
gctgggatat catcatatac tg                                              22

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
cggactagta catcatctat actg                                            24

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ggatgcagaa gagaactcca                                                 20

<210> SEQ ID NO 207
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
cctcatcctg tgagccag                                                   18

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ttgagaactg aattccatgg                                                 20

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
```

```
gctgaagaac tgaatttcag ag                                              22
```

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210

```
ctaaagacaa catttctgca cac                                             23
```

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211

```
atctagcaga agcatttcca c                                               21
```

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212

```
gaggaagaca gcacgtttgg t                                               21
```

<210> SEQ ID NO 213
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213

```
aaaggcgcag cgacgt                                                     16
```

<210> SEQ ID NO 214
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214

```
tctgtctaag tcacccaatc tc                                              22
```

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215

```
tctattcttc cctcccactc                                                 20
```

```
<210> SEQ ID NO 216
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
ctggctccgt gtcttcact                                                      19

<210> SEQ ID NO 217
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
agcacagccc ccgtcc                                                         16

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gtctcccaac ccttgtacca g                                                   21

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tgtcccccag gcctgtac                                                       18

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ctcgaggagc tcacagtcta g                                                   21

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
gtcctcaagg agcttcagtc                                                     20

<210> SEQ ID NO 222
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
gcccaggttc tgtgatacac t                                              21

<210> SEQ ID NO 223
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
cccaagttct gtcatgcac                                                 19

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224 cattttgtg atctgcagct agt                                             23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
tcacttttgt gactatgcaa ctg                                            23

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
taggttatcc gtgttgcctt                                                20

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
aataggtcaa ccgtgtatga ttc                                            23

<210> SEQ ID NO 228
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 228
gttaatgcta atcgtgatag gg                                                22

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gctaatatgt aggagtcagt tgga                                              24

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
aacattcaac gctgtcggt                                                    19

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cagtcaacgg tcagtggttt                                                   20

<210> SEQ ID NO 232
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
aacattcaac gctgtcggt                                                    19

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ttgcattcat tgttcagtga g                                                 21

<210> SEQ ID NO 234
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 234
tttggcaatg gtagaactca c                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
gttggcaagt ctagaaccac c                                              21

<210> SEQ ID NO 236
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
gtatggcact ggtagaattc ac                                             22

<210> SEQ ID NO 237
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
tatggccctt cggtaattc                                                 19

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
cttatcactt ttccagccca                                                20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
ccttatcagt tctccgtcca                                                20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      primer <210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 240
ggagagaaag gcagttcctg                                              20

<210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 241
ggaccagagg aaagccag                                                18

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 242
cacccatcat attcttccca                                              20

<210> SEQ ID NO 243
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 243
gacattcaca tgcttcaggt ag                                           22

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 244
ctcgggctac aacacagga                                               19

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 245
gctgcaacac aagacacga                                               19

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 246
ccatatgtcg tgccaagaga                                              20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
cacatgcaca agagagcaag                                              20

<210> SEQ ID NO 248
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
gtgatatgtt tgatatatta ggttg                                        25

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
ggaatatgtt tgatatatag ttgg                                         24

<210> SEQ ID NO 250
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
gcaacggaat cccaaaag                                                18

<210> SEQ ID NO 251
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gacgaaatcc aagcgca                                                 17

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
ctgacctatg aattgacagc c                                            21

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
tgacctatgg aattggcag                                                    19

<210> SEQ ID NO 254
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gtctttgcgg gcgagat                                                      17

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
aactgggact ttgtaggcca                                                   20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
tgtaacagca actccatgtg                                                   20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
taacagcatc tccactggaa                                                   20

<210> SEQ ID NO 258
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
ggagtctttg ttgcccaca                                                    19

```
<210> SEQ ID NO 259
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ggctcagccc ctcctc                                                       16

<210> SEQ ID NO 260
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
taggtagttt catgttgttg gg                                                22

<210> SEQ ID NO 261
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
atcgggtggt ttaatgttg                                                    19

<210> SEQ ID NO 262
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
taccacccgg tacagga                                                      17

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
cagtttcttg ttgccgagtt                                                   20

<210> SEQ ID NO 264
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
attgcccgct gtgga                                                        15

<210> SEQ ID NO 265
<211> LENGTH: 17
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
aggcagtgtc gtgctgt                                                    17

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
ctgtgccggg tagagagg                                                   18

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
atgctgggtg gagaaggt                                                   18

<210> SEQ ID NO 268
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ggtccagagg ggagata                                                    17

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
tttattctat agagaagaag gaaa                                            24

<210> SEQ ID NO 270
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
gtggtggttt ccttggct                                                   18

<210> SEQ ID NO 271
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 271
ggtggtggaa aatgacactc                                               20

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
ggaggctttt cctgaggac                                                19

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
ccctagtgtg caaaacctgt                                               20

<210> SEQ ID NO 274
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
caccggatgg acagaca                                                  17

<210> SEQ ID NO 275
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
cggtccagct ctccagt                                                  17

<210> SEQ ID NO 276
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
ttccacagca gcccctg                                                  17

<210> SEQ ID NO 277
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
                         primer

<400> SEQUENCE: 277
gatgtgcctc ggtggtgt                                                    18

<210> SEQ ID NO 278
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
catcttactg ggcagcattg                                                  20

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
gtcatcatta ccaggcagta ttag                                             24

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
ctcgtcttac ccagcagtgt                                                  20

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
gtcatcatta ccaggcagta ttag                                             24

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
tccagtggtt cttaacagtt ca                                               22

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 283
ggtctagtgg tcctaaacat ttc                                    23

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
ccctttgtca tcctatgcct                                        20

<210> SEQ ID NO 285
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gtccctttgc cttccca                                           17

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
ccttcattcc accggagt                                          18

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
gaacttcact ccactgaaat ctg                                    23

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
acatgcttct ttatatcccc a                                      21

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
```

```
aaaccacaca cttccttaca ttc                                              23
```

<210> SEQ ID NO 290
<211> LENGTH: 17
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 290

```
agcttttggc ccgggtt                                                     17
```

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 291

```
ccaacaagct ttttgctcgt c                                                21
```

<210> SEQ ID NO 292
<211> LENGTH: 17
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 292

```
cctgcccacc gcacact                                                     17
```

<210> SEQ ID NO 293
<211> LENGTH: 17
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 293

```
agccgctgtc acacgca                                                     17
```

<210> SEQ ID NO 294
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 294

```
cctttgtcat ccttcgcct                                                   19
```

<210> SEQ ID NO 295
<211> LENGTH: 17
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 295

```
cccctttgct gtccctg                                                     17
```

```
<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
caccttggct ctagactgct t                                              21

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
gccgtgactg gagactgtta                                                20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
gaacattcaa cgctgtcggt                                                20

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
gtacaatcaa cggtcgatgg t                                              21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tctgcctgtc tacacttgct g                                              21

<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
tgactgcctg tctgtgcct                                                 19

<210> SEQ ID NO 302
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
atgacctatg aattgacaga caat                                            24

<210> SEQ ID NO 303
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
ttggcctaaa gaaatgacag ac                                              22

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
tggcttaatc tcagctggca                                                 20

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
tgagggctag gaaattgctc t                                               21

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
gatactgcat caggaactga ttg                                             23

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
ggcaatgcat taggaactga t                                               21

<210> SEQ ID NO 308
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 308
gtgcttgatc taaccatgtg gt                                              22

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
gtgcttgacg gaaccatgtt                                                 20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
tcctgattgt ccaaacgcaa                                                 20

<210> SEQ ID NO 311
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gggacgtcca gactcaactc tc                                              22

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
ccacaccgta tctgacactt t                                               21

<210> SEQ ID NO 313
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
cagaccgcat catgaacac                                                  19

<210> SEQ ID NO 314
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 314
cctggcatac aatgtagatt tctg                                          24

<210> SEQ ID NO 315
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
aaacccagca gacaatgtag ct                                            22

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
ccccagaagg caaaggat                                                 18

<210> SEQ ID NO 317
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
ctctctcagg acactgaagc ag                                            22

<210> SEQ ID NO 318
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
ccgtgtattt gacaagctga gt                                            22

<210> SEQ ID NO 319
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
tggggtattt gacaaactga ca                                            22

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
ggctttcaag tcactagtgg ttc                                        23

<210> SEQ ID NO 321
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
ctttgtagtc actagggcac ca                                         22

<210> SEQ ID NO 322
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322 cccccctca atcctgt                                                17

<210> SEQ ID NO 323
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ggagagcctc cacccaac                                              18

<210> SEQ ID NO 324
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
accaccatcg tgcggta                                               17

<210> SEQ ID NO 325
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
gtttggatgg ctgggct                                               17

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
gctctgactt tattgcacta ctg                                              23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
gctttgacaa tactattgca ctg                                              23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
ccacttaaac gtggatgtac ttg                                              23

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
tcaccaaaac atggaagcac                                                  20

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
caactttaac atggaagtgc ttt                                              23

<210> SEQ ID NO 331
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
cctactaaaa catggaagca cttac                                            25

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
gctttaacat gggggtacct                                                  20

```
<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
tcaccaaaac atggaagcac                                              20

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
tctactttaa catggaggca ctt                                          23

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
tcaccaaaac atggaagcac                                              20

<210> SEQ ID NO 336
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
cgccttctct tcccggt                                                 17

<210> SEQ ID NO 337
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
ttcgccctct caaccca                                                 17

<210> SEQ ID NO 338
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
ctaagccagg gattgtggg                                               19
```

```
<210> SEQ ID NO 339
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
ctttaccccg ggtggg                                                    16

<210> SEQ ID NO 340
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
agaggtggtc cgtggcg                                                   17

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gaggtcgacc gtgtaatgtg c                                              21

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
cattgctgtc tctcttcgca                                                20

<210> SEQ ID NO 343
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
tggggctttc ttcccag                                                   17

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
cctagtaggt gtccagtaag tgt                                            23

<210> SEQ ID NO 345
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
gataggaggt cctcaataaa ca                                          22

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
cgggactccc atcaagaa                                               18

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
ctggaagctg aagctgcat                                              19

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
gaggggctca gggagaaag                                              19

<210> SEQ ID NO 349
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
ggacggaagg gcagaga                                                17

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
ctgggcctgt gtcttaggct                                             20

<210> SEQ ID NO 351
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 351
tgcaggccgt gtgcttt                                                    17

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
gagctgaaag cactcccaa                                                  19

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
cacactcttg atgttccagg a                                               21

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
gtcaagagca ataacgaaaa atg                                             23

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
gaggtcagga gcaataatga a                                               21

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
acggcttcat acaggagttg                                                 20

<210> SEQ ID NO 357
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 357
ggcatcatat aggagctgga                    20

<210> SEQ ID NO 358
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
ccaacaatat cctggtgctg ag                 22

<210> SEQ ID NO 359
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
caacaaaatc actgatgctg ga                 22

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
tccctgtcct ccaggagct                     19

<210> SEQ ID NO 361
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
tctgtcgtcg aggcgct                       17

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
ataaagcaat gagactgatt gtc                23

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 363
ggctataaag taactgagac gga                                              23

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gtgctatctg tgattgaggg a                                                21

<210> SEQ ID NO 365
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
cgggtgcgat ttctgtg                                                     17

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
ctgactccta gtccagggct                                                  20

<210> SEQ ID NO 367
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
ctccagaccc ctcgttca                                                    18

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
gcatgcctgc ctctctgttg                                                  20

<210> SEQ ID NO 369
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 369

```
tgcccaggca gctgca                                                    16

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
cttatcagaa tctccagggg tac                                            23

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
gcaaatcaga atcacacctg                                                20

<210> SEQ ID NO 372
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
ctgttgctaa tatgcaactc tg                                             22

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
caccattgct aaagtgcaat                                                20

<210> SEQ ID NO 374
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
ggtggatatt ccttctatgt ttatg                                          25

<210> SEQ ID NO 375
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
aacgtggaat ttcctctatg tt                                             22
```

```
<210> SEQ ID NO 376
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
ggagatcgac cgtgttatat tc                                              22

<210> SEQ ID NO 377
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
gaaaagatca accatgtatt attcg                                           25

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
ggtcacgtct ctgcagttac a                                               21

<210> SEQ ID NO 379
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
accaggttcc accccag                                                    17

<210> SEQ ID NO 380
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
tcaaactgtg ggggcactt                                                  19

<210> SEQ ID NO 381
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
acactcaaaa gatggcggc                                                  19

<210> SEQ ID NO 382
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
gcctcaaatg tggagcacta tt                                              22

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
tcaaatgtcg cagcactttc                                                 20

<210> SEQ ID NO 384
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
ctcaaaatgg gggcgctt                                                   18

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
caccccaaaa tcgaagcact                                                 20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
gccctcaagg agctcacagt                                                 20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387 cacccctgg gaagaaattt                                                  20

<210> SEQ ID NO 388
<211> LENGTH: 16
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 388
acgagcccct cgcaca                                                         16

<210> SEQ ID NO 389
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
cctcacgcga gccgaac                                                        17

<210> SEQ ID NO 390
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
ggtagattct ccttctatga gtac                                                24

<210> SEQ ID NO 391
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
acgtggattt tcctctatg                                                      19

<210> SEQ ID NO 392
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
gagcagaggt tgcccttg                                                       18

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393
acaaaagttg cctttgtgtg a                                                   21

<210> SEQ ID NO 394
<211> LENGTH: 20
<212> TYPE: DNA
<213> ORGANISM: Artificial Sequence
<220> FEATURE:

-continued

<223> OTHER INFORMATION: Description of Artificial Sequence: Synthetic
     primer

<400> SEQUENCE: 394
ctcctgactc caggtcctgt                                              20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 395
gccttctgac tccaagtcca                                              20

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 396
agagatggta gactatggaa cgt                                          23

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 397
gtggaccatg ttacataggt cag                                          23

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 398
gatggttgac catagaacat g                                            21

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 399
gatgtggacc atattacata cga                                          23

<210> SEQ ID NO 400
<211> LENGTH: 17
<212> TYPE: DNA
<213> ORGANISM: Artificial Sequence
<220> FEATURE:
<223> OTHER INFORMATION: Description of Artificial Sequence: Synthetic
     primer

```
<400> SEQUENCE: 400
agcgaggttg ccctttg                                                17

<210> SEQ ID NO 401
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
acagagagct tgcccttgta ta                                          22

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
gaagttgttc gtggtggatt c                                           21

<210> SEQ ID NO 403
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
aagtgttgtc cgtgaatgat tc                                          22

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
cagatcagaa ggtgattgtg gct                                         23

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 405
ttctgaccag gcagtgctgt                                             20

<210> SEQ ID NO 406
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 406
```

```
caattcctag acaatatgta taatg                                              25
```

<210> SEQ ID NO 407
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 407

```
gtcattccta gaaattgttc ata                                                23
```

<210> SEQ ID NO 408
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 408

```
tcctgactcc aggtcctgt                                                     19
```

<210> SEQ ID NO 409
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 409

```
ggccttctga ctccaagtc                                                     19
```

<210> SEQ ID NO 410
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 410

```
tgaggggcag agagcga                                                       17
```

<210> SEQ ID NO 411
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 411

```
gagggggcctc agaccga                                                      17
```

<210> SEQ ID NO 412
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 412

```
agcagcaatt catgttttga ag                                                 22
```

<210> SEQ ID NO 413
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 413
gcagcgcctc acgtttt                                                    17

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 414
atgacacgat cactcccgtt g                                               21

<210> SEQ ID NO 415
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 415
gggcggacac gacattc                                                    17

<210> SEQ ID NO 416
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 416
aggtagtagg ttgtatagtt ttagg                                           25

<210> SEQ ID NO 417
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 417
taggaaagac agtagattgt atagt                                           25

<210> SEQ ID NO 418
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 418
cctggatgtt ctcttcactg                                                 20

```
<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 419
gcctggatgc agactttct                                               20

<210> SEQ ID NO 420
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 420
gaggtagtag gttgtatagt ttagaa                                       26

<210> SEQ ID NO 421
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 421
aaagctagga ggctgtaca                                               19

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 422
ttccagccat tgtgactgca                                              20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 423
ctcaccatgt tgtttagtgc                                              20

<210> SEQ ID NO 424
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 424
gaggtagtag gttgtatagt ttgg                                         24

<210> SEQ ID NO 425
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 425
ggaaagacag tagattgtat agttat                                          26

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 426
accaagaccg actgcccttt                                                 20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 427
ctctgtccac cgcagatatt                                                 20

<210> SEQ ID NO 428
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 428
tgaggtagta ggttgtgtgg t                                               21

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 429
ggaaggcagt aggttgtata g                                               21

<210> SEQ ID NO 430
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 430
cctcccgcag tgcaag                                                     16

<210> SEQ ID NO 431
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 431
catggggtcg tgtcactg                                                    18

<210> SEQ ID NO 432
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 432
ttgaggtagt aggttgtatg gtt                                              23

<210> SEQ ID NO 433
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 433
ggaaagctag aaggttgtac ag                                               22

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 434
ttggaggagc tgactgaaga                                                  20

<210> SEQ ID NO 435
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 435
aagaattcct cgacggctc                                                   19

<210> SEQ ID NO 436
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 436
aggttgcata gttttagggc a                                                21

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
    primer

<400> SEQUENCE: 437
aaggcagcag gtcgtatagt                                              20

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
gccaagtaga agaccagcaa g                                            21

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
caaggaaaca ggttatcggt g                                            21

<210> SEQ ID NO 440
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
gaggtaggag gttgtatagt tgag                                         24

<210> SEQ ID NO 441
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
gaaagctagg aggccgtata g                                            21

<210> SEQ ID NO 442
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
ctgtctgtct gtctgtc                                                 17

<210> SEQ ID NO 443
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 443
agaaaagagc ccggctctt                                                19

<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 444
gattgtatag ttgtggggta gtg                                           23

<210> SEQ ID NO 445
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 445
gggaaggcaa tagattgtat ag                                            22

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 446
tgtactttcc attccagaag                                               20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 447
taatgcagca agtctactcc                                               20

<210> SEQ ID NO 448
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 448
ggtagtagat tgtatagttt taggg                                         25

<210> SEQ ID NO 449
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 449
```

```
gggaaagaca gtagactgta tagt                                          24

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 450
tgaagatgga cactggtgct                                               20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 451
cagtcggaga agaagtgtac                                               20

<210> SEQ ID NO 452
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 452
gtagtagttt gtacagtttg agggt                                         25

<210> SEQ ID NO 453
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 453
ggcagtggcc tgtacagt                                                 18

<210> SEQ ID NO 454
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 454
agcgctccgt ttcctttt                                                 18

<210> SEQ ID NO 455
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 455
ccccacttgg cagctg                                                   16
```

```
<210> SEQ ID NO 456
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 456
tgtgctgttg gtcgggt                                                  17

<210> SEQ ID NO 457
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
gcagtagctt gcgcagtt                                                 18

<210> SEQ ID NO 458
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
cgaggaagga cggagga                                                  17

<210> SEQ ID NO 459
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 459
gctgagcatc accagcac                                                 18

<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 460
gtagcagcac ataatggttt gtg                                           23

<210> SEQ ID NO 461
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 461
cagcagcaca gttaaatact ggag                                          24

<210> SEQ ID NO 462
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 462
gggctttaaa gtgcaggg                                                 18

<210> SEQ ID NO 463
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
cacccaccac tgg                                                      13

<210> SEQ ID NO 464
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
ctctgccctg ctatg                                                    15

<210> SEQ ID NO 465
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
agtgatgttg cccc                                                     14

<210> SEQ ID NO 466
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 466
agttacaccc tggga                                                    15

<210> SEQ ID NO 467
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 467
attttgccca caagga                                                   16

<210> SEQ ID NO 468
<211> LENGTH: 15
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 468
acacccaagg agatc                                                          15

<210> SEQ ID NO 469
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 469
ttaccctgtt caggag                                                         16

<210> SEQ ID NO 470
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 470
taccccatct tggag                                                          15
```

METHODS FOR QUANTIFYING MICRORNA PRECURSORS

REFERENCE TO RELATED APPLICATION

This application claims priority from U.S. Provisional Application Ser. No. 60/656,109, filed Feb. 24, 2005, the entire content of which is incorporated herein by reference.

STATEMENT OF GOVERNMENT SUPPORT

This invention is supported, at least in part, by Grant No. CA107435 from the National Institutes of Health, USA. The U.S. government has certain rights in this invention.

BACKGROUND

Mature microRNAs[1] (miRNAs) are endogenous, ~21 nucleotide (nt), non-coding RNAs whose primary function is believed to be translational repression of protein coding mRNAs. The mature miRNA is processed from longer precursor molecules by the enzymes drosha and Dicer.

[1] The abbreviations used are: cDNA, complementary DNA; C. elegans, Caenorhabditis elegans; CLL, chronic lymphocytic leukemia; LMW, low molecular weight; miRNA, microRNA; mRNA, messenger RNA; nt, nucleotides; PCR, polymerase chain reaction; pri-miRNA, primary microRNA precursor; RT-PCR, reverse transcriptase polymerase chain reaction; Tm, melting temperature.

miRNAs have been found in *C. elegans*, *Drosophila*, plants, mice and humans, suggesting an ancient and widespread role for these non-coding RNAs. To date, over 3,500 miRNAs have been discovered, including 114 in *C. elegans*, 332 in humans and 270 in mice. An algorithm termed miRscan was developed to predict the number of miRNAs in a genome based upon the phylogenetically conserved foldback structure of the miRNA. miRscan predicts that the total number of miRNAs in the human genome to be 200-255, or about 1% of the predicted genes in humans.

The founding members of the miRNA class of genes, lin-4 and let-7, are expressed temporally during development of *C. elegans*. In addition to regulating development in *C. elegans*, miRNAs have been shown to negatively regulate the proapoptotic gene hid during *Drosophila* development. Thus, levels of miRNA or miRNA precursors in samples taken from *C. elegans* or *Drosophila* can be used to determine the stage of development of these two organisms.

miRNAs are also associated with various diseases. For example, two human miRNAs (miR-15a and miR-16) have been mapped to the region 13q14 that is commonly deleted in chronic lymphocytic leukemia (CLL). The expression of miR-15a and miR-16 is reduced in CLL patients with loss of heterozygosity at 13q14.

Thus, the levels of miRNA and their precursors in samples taken from a test subject, including human subjects, can be used to study the role of miRNAs in health and disease and to identify drugs that modulate miRNA function.

Most of the miRNA expression data published to date have used Northern blotting to detect both the mature and pre-miRNA precursors. Probes designed to hybridize to the mature miRNA detect the ~22 nt mature miRNA and the ~75 nt pre-miRNA simultaneously on the blot. Primer extension has also been effectively used to detect the mature miRNA. As tools for monitoring gene expression, gel based assays (Northern blotting, primer extension, RNase protection assays, etc.) have disadvantages, including low throughput and poor sensitivity.

cDNA microarrays are an alternative to Northern blotting to quantify miRNAs since microarrays have excellent throughput. For example, a recent report used cDNA microarrays to monitor the expression of miRNAs during neuronal development. Microarrays have other disadvantages including the necessity for high concentrations of input target for efficient hybridization and signal generation, poor sensitivity for rare targets and the necessity for post-array validation using more sensitive assays such as real-time PCR.

A PCR approach has been used to determine the expression levels of mature miRNAs. This method, while useful to clone miRNAs, is impractical for routine gene expression studies since it involves gel isolation of small RNAs and ligation to linker oligonucleotides. PCR has also been used to measure the expression of primary miRNA precursor molecules.

Because of the short size of miRNAs and the sequence similarity between miRNA family members, new and different methods are needed to detect and quantify their expression. Additionally, it is desirable to analyze the expression levels of miRNA precursors. For example, miRNA precursor levels can provide an indirect method of analyzing the expression levels of mature miRNAs. Studying the differential expression of different miRNA precursors as compared to the mature miRNA is itself of interest. For example, certain disease processes may interfere with different steps during the processing of miRNA precursors.

Therefore, a need exists for a high throughput method that allows for the simultaneous analysis of miRNA precursor molecules and that provides for the analysis of miRNA expression when only small amounts of starting material are available.

SUMMARY OF THE PRESENT INVENTION

In general, the invention relates to methods and compositions for detecting both pri-microRNA and pre-microRNA precursors in a sample. The method involves detection of a portion of the hairpin sequence that is shared by both the pri-miRNA and the pre-miRNA In a first aspect, the method uses a gene-specific reverse primer to reverse transcribe a targeted portion of said hairpin sequence.

In another aspect, the method uses gene-specific forward and reverse primers in an amplification reaction to amplify the targeted portion of the hairpin sequence.

In another aspect, the invention features a method for identifying differential expression of hairpin-containing microRNA precursors in a test sample. The method includes performing an amplification reaction on the test sample to amplify a target nucleotide sequence wherein the target nucleotide sequence includes a portion of the hairpin sequence that is longer than the mature microRNA sequence. The method also includes detectably labeling the target nucleotide sequence and detecting a difference between the amount of the detectably labeled target nucleotide sequence present in the test sample relative to a corresponding control.

In another aspect, the invention features a method for detecting a first microRNA precursor in a sample that contains at least a second microRNA precursor that is an isoform of the first microRNA precursor. The first and second microRNA precursor isoforms have hairpin sequences that are substantially similar, including substantially similar primer portions that bind the forward and reverse primers of the present invention. The method includes performing an amplification reaction on the sample to produce a first amplification product containing the hairpin sequence of the first microRNA precursor, and a second amplification product containing the hairpin sequence of the second microRNA precursor. The amplification reaction is performed using a forward primer and a reverse primer targeted to the substantially similar primer portions of the hairpin sequences of the first and the second microRNA precursors. The method also includes detecting only the first amplification product using a sequence-specific detection probe targeted to a sequence that is unique to the hairpin sequence of the first microRNA precursor, wherein the unique sequence lies between the substantially similar primer portions of the hairpin sequences.

BRIEF DESCRIPTION OF THE FIGURES

FIG. 10. Table representing the intra-assay variation from replicate RNA isolations.

FIG. 11. Table showing the efficiency of amplification for miRNA genes using U6 RNA.

FIG. 12. Primer and TaqMan® probe sequences to let-7 miRNA isoforms (SEQ ID NOS 3-21 and 11-12, respectively, in order of appearance). (A) The sequences of the miRNA precursors for the members of the human let-7 family of miRNA isoforms. Line above sequence, sequence of the mature miRNA; Dashed underlined, sequences of the forward PCR primers; Boxed, sequences of the reverse PCR primers; Bold: priming sequences that differ among isoforms. Also shown are sequences of the human let-7 family mature miRNAs. (B) The sequence of the TaqMan® MGB probe is double-underlined. Sequences are in the 5' to 3' direction.

FIG. 15. PCR Primers (SEQ ID NOS 22-261, 260, 263, 260 and 265-459, respectively, in order of appearance) used to amplify the human miRNAs precursors. p, primers to miRNA primary precursor sequence. All other primers hybridize to hairpin present in both the primary precursor and precursor miRNA.

DETAILED DESCRIPTION OF THE INVENTION

The present invention provides methods and compositions for the analysis of microRNA precursor expression and will now be described with reference to more detailed examples. The examples illustrate how a person skilled in the art can make and use the invention, and are described here to provide enablement and best mode of the invention without imposing limitations that are not recited in the claims.

All publications, patent applications, patents, internet web pages and other references mentioned herein are expressly incorporated by reference in their entirety. When the definitions of terms in incorporated references appear to differ from the definitions provided in the present teachings, the definitions provided in the present teachings shall control.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Figure 1:
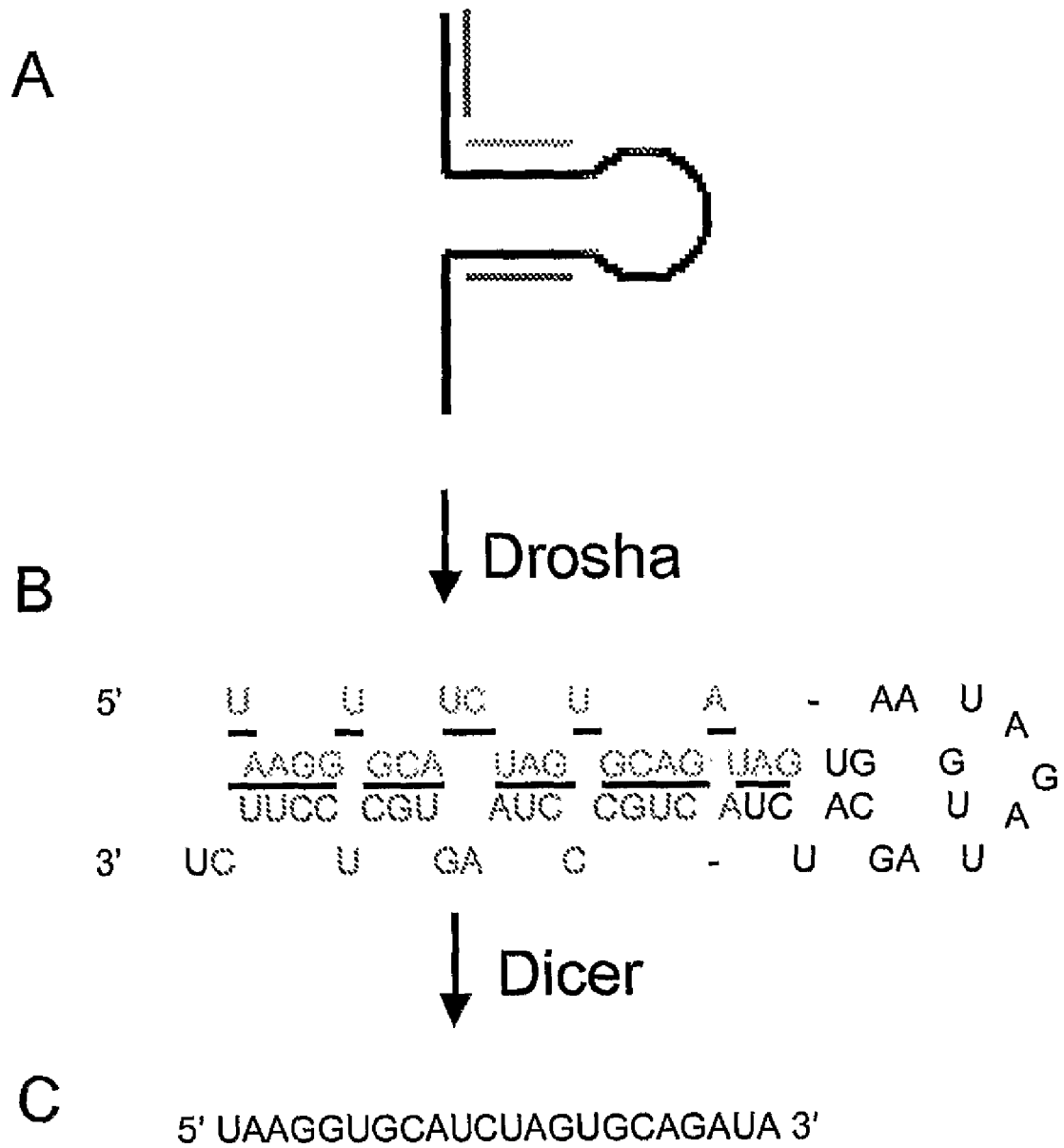
FIG. 1. miRNA processing and primer design. miRNAs such as human miR-18 are transcribed as a (A) large primary precursor (pri-miRNA) that is processed by the nuclear enzyme Drosha to produce the (B) putative 62 nt precursor miRNA (pre-miRNA) (SEQ ID NO: 1). Both the pri-miRNA and pre-miRNA contain the hairpin structure. The underlined portion of the pre-miRNA represents the sequence of the (C) 22 nt mature miRNA (SEQ ID NO: 2) that is processed from the pre-miRNA by the ribonuclease Dicer. Gray line denotes forward primer; Black line denotes reverse primer; Dashed line denotes sense primer used along with the reverse (black) primer to amplify the pri-miRNA only.

The following introduction is useful for understanding the terms used in this description. Without being bound to the following theory and with reference to FIG. 1, it is believed that miRNAs are encoded by genes that are transcribed into single or clustered miRNA precursors. These miRNA precursors are converted to mature forms of miRNAs through a stepwise processing, as depicted in FIG. 1. It is believed that the processing first generates (A) a large ~70 nucleotide (nt) primary precursor, referred to herein as a "pri-miRNA," that is then processed by the nuclear enzyme Drosha to produce (B) a putative ~62 nt precursor, referred to herein as a "pre-miRNA." Both the pri-miRNA and pre-miRNA contain a characteristic hairpin structure. The underlined portion of the pre-miRNA sequence in FIG. 1 represents the sequence of (C) the ~22 nt mature miRNA that is processed from the pre-miRNA by the ribonuclease Dicer. Thus the term "pri-microRNA" refers to molecule A, "pre-miRNA" refers to molecule B, "mature miRNA" refers to molecule C, and "miRNA precursor(s)" refers to both pri- and pre-miRNAs (i.e. molecules A and B), as shown in FIG. 1.

Still referring to FIG. 1, both the pri-miRNA and pre-miRNA molecules have a "hairpin sequence," which is an oligonucleotide sequence having a first half which is at least partially complementary to a second half thereof, thereby causing the halves to fold onto themselves, forming a "hairpin structure." The hairpin structure is typically made of a "stem" part, which consists of the complementary or partially complementary sequences, and a "loop" part, which is a region located between the two complementary strands of the stem, as depicted in FIG. 1.

Provided herein are methods and kits for detecting the expression levels of both the pri- and the pre-miRNA precursor in a test sample using gene-specific primers targeted to a portion of the hairpin sequence shared by both the pri- and the pre-miRNA precursors. The term "target nucleotide sequence" or "target nucleotide" as used herein, refers to the polynucleotide sequence that is sought to be detected, i.e. the sequence that is targeted by the gene-specific primers of the present invention. The target nucleotide sequence, as used herein, comprises a portion of the hairpin sequence which is shared by both the pri- and the pre-miRNA precursors and may comprise the entire hairpin sequence. Alternative, the target nucleotide sequence may comprise only a portion of the hairpin sequence which portion is substantially longer than the mature miRNA sequence and is typically about 70 nucleotides long. In either case, the target nucleotide sequence may include a few nucleotides beyond the hairpin sequence, so long as the target nucleotide sequence is shared by the pri- and pre-miRNA precursors. Target nucleotide sequence is intended to include DNA (e.g., cDNA or genomic DNA), RNA, analogs of the DNA or RNA generated using nucleotide analogs, and derivatives, fragments and homologs thereof.

The methods described generally employ a two step approach. First, the target nucleotide sequence of the miRNA precursors is reverse transcribed into cDNA using a gene-specific reverse primer and a thermostable reverse transcriptase. Second, the target nucleotide sequence cDNA is amplified and detected, thereby simultaneously detecting the expression levels of both the pri- and the pre-miRNA molecules in the test sample. Alternatively, the methods may be applied directly on genomic DNA without the need for reverse transcription.

In some embodiments, the target nucleotide sequence cDNA acts as a template in an amplification reaction. Amplification products are then detected using detection probes. As used herein, the term "amplifying" or "amplification reaction" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary means for performing an amplifying step include PCR, primer extension, ligase chain reaction (LCR), ligase detection reaction (LDR), ligation followed by Q-replicase amplification, strand displacement amplification (SDA), hyperbranched strand displacement amplification, multiple displacement amplification (MDA), nucleic acid strand-based amplification (NASBA), two-step multiplexed amplifications, rolling circle amplification (RCA), in vitro transcription using a forward primer containing a promoter sequence for RNA polymerase and the like, including multiplex versions or combinations thereof. Descriptions of such techniques can be found in, among other places, Sambrook et al. Molecular Cloning, 3rd Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1): 41-7, U.S. Pat. No. 6,027,998; U.S. Pat. No. 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol. Diagn. 2002 November; 2(6):542-8, Cook et al., J Microbiol Methods. 2003 May; 53(2):165-74, Schweitzer et al., Curr Opin Biotechnol. 2001 February; 12(1):21-7, U.S. Pat. No. 5,830,711, U.S. Pat. No. 6,027,889, U.S. Pat. No. 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a gene-specific primer that is annealed to a template and extended in the 5' to 3' direction using an amplifying means such as a polymerase and/or reverse transcriptase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed linker probe, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carryover of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol. Biotechnol. 2004 February; 26(2):13346. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536,649, and U.S. Provisional Application 60/584,682 to Andersen et al.). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Stoflet E S, Koeberl D D, Sarkar G, Sommer S S, Genomic amplification with transcript sequencing, Science 239(4839):491-4 (1988).

In some embodiments, detector probes are used to detect amplified target nucleotides. As used herein, the term "detector probe" refers to a molecule used in an amplification reaction, typically for quantitative or real-time PCR analysis, as well as end-point analysis. Such detector probes can be used to monitor the amplification of the target polynucleotide. In some embodiments, detector probes present in an amplification reaction are suitable for monitoring the amount of amplicon(s) produced as a function of time. Such detector probes include, but are not limited to, the 5'-exonuclease assay (TaqMan® probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons® (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), Sunrise®/Amplifluor® probes (U.S. Pat. No. 6,548,250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescein dyes with $SO_3$ instead of the carboxylate group, phosphoramidite forms of fluorescein, phosphoramidite forms of CY 5 (commercially available for example from Amersham). In some embodiments, intercalating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, probes further comprise various modifications such as a minor groove binder (see for example U.S. Pat. No. 6,486,308) to further provide desirable thermodynamic characteristics.

In some embodiments, the target nucleotide cDNA can be detected using a variety of hybridization techniques. As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementary sequence, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings. Novel hybridization techniques, such as bead-based flow cytometry (described for example in Lu J, et al., MicroRNA expression profiles classify human cancers, Nature. 2005 Jun. 9; 435(7043):834-8) are also contemplated by the present teachings.

In some embodiments, the 3' gene-specific primer can be used in an extension reaction. As used herein, the term "extension reaction" refers to an elongation reaction in which the 3' gene-specific primer is extended to form an extension reaction product comprising a strand complementary to the target polynucleotide. In some embodiments, the target polynucleotide is a portion of the hairpin sequence common to both a pri- and a pre-miRNA molecule and the extension reaction is a reverse transcription reaction comprising a reverse transcriptase. In some embodiments, the extension reaction is a reverse transcription reaction comprising a polymerase derived from a Eubacteria. In some embodiments, the extension reaction can comprise rTth polymerase. It will be appreciated that the use of polymerases that also comprise reverse transcription properties can allow for some embodiments of the present teachings to comprise a first reverse transcription reaction followed thereafter by an amplification reaction, thereby allowing for the consolidation of two reactions in essentially a single reaction. In some embodiments, the consolidation of the extension reaction and a subsequent amplification reaction is further contemplated by the present teachings.

As used herein, the term "detection" refers to any of a variety of ways of determining the presence and/or quantity and/or identity of a target polynucleotide. In some embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, Texas Red (Molecular Probes) and the group Vic™, Liz™, Tamra™, 5-Fam™, 6-Fam™ (all available from Applied Biosystems, Foster City, Calif.). In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System the ABI GeneAmp® Sequence Detection System series (all available from Applied Biosystems, Foster City, Calif.), or the LightCycler® (Roche Diagnostics, Indianapolis, Ind.) In some embodiments, each of these functions can be performed by separate devices. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification. In some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide. As used herein, determining the presence of a target can comprise identifying it, as well as optionally quantifying it.

In some embodiments, different detector probes may distinguish between different target polynucleotides. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different hairpin sequences of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' may form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B. In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target polynucleotide determined via a mobility dependent analysis technique of the eluted mobility probes, as described for example in Published P.C.T. Application WO04/46344 to Rosenblum et al., and WO01/92579 to Wenz et al. In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:14045, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

The term "corresponding" as used herein refers to a specific relationship between the elements to which the term refers. Some non-limiting examples of corresponding include: a gene-specific forward or reverse primer can correspond with a target polynucleotide, and vice versa. A detector probe can correspond with a particular region of a target polynucleotide and vice versa. In some cases, the corresponding elements can be complementary. In some cases, the corresponding elements are not complementary to each other, but one element can be complementary to the complement of another element. The term corresponding is also used when referring to the pri-miRNA and the pre-miRNA molecules that belong to one miR gene.

The term "sample" as used herein refers to any sample that contains the target nucleotide sequence and can be obtained from any organism known to contain miRNA encoding genes. In certain examples, the sample is obtained from a mammal, such as a human or mouse. In other embodiments, the sample is derived from other organisms, such as a plant, *C. elegans* or *drosophila*. It will be appreciated that the target nucleotide sequence can be isolated from samples using any of a variety of procedures known in the art.

The term "pair of primers targeted to" a target nucleotide sequence refers to forward and reverse primers that can anneal to either end of the target nucleotide sequence. It is appreciated by those skilled in the art that a forward (or sense) primer can usually directly hybridize to a first primer portion located at the 5' end of the target nucleotide sequence, while a reverse (or anti-sense) primer can hybridize to the complement of the second primer portion located at the 3' end of the target nucleotide sequence.

The term "primer portion" refers to a region of a polynucleotide sequence that can serve directly, or by virtue of its complement, as the template upon which a primer can anneal for any of a variety of primer nucleotide extension reactions known in the art (for example PCR).

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

In the presented examples, detection of hairpin-containing miRNA precursor levels is achieved by (a) converting the pri- and pre-miRNA precursors to cDNA using a gene-specific reverse primer and a reverse transcriptase, and (b) amplifying and detecting a portion of the hairpin sequence common to the pri- and pre-miRNA precursors. In each amplification reaction, the forward and reverse primers are targeted to amplify a substantial portion of the hairpin sequence. In one example, the forward primer is targeted to a sequence located at the 5' end of the hairpin structure and the reverse primer is targeted to a sequence located at the 3' end of the hairpin structure.

Appropriate primers can be designed using the following criteria. Both forward and reverse primers are designed to be located within or substantially within the hairpin sequence of the miRNA precursors (FIG. 1). The pre-miRNA sequences are predicted based upon the fold-back structure. Sequences of known precursor miRNA precursor species are available on the miRNA registry (http://www.sanger.ac.uk/Software/Rfam/mirna/index.shtml) (Griffiths-Jones, S., The microRNA Registry. Nucleic Acids Res, 2004. 32(1): p. D109-11.) An extension of about 4 nucleotides is allowed for each primer over the presumed 5' or 3' termini of the pre-miRNA. It is understood, however, that different length primers can be used as long as the target nucleotide amplified by the primers is shared between the pri- and the pre-miRNA precursors.

Since the hairpin is contained within both the pri-miRNA and the pre-miRNA, primers designed to the hairpin simultaneously amplify both RNAs. Primers are designed with a maximal $T_m$ difference between both primers of $\leq 2°$ C. and an optimal primer length between 16-24 nucleotides for primers composed of the identical chemical composition of natural DNA. The primers have a Tm range of 48-62° C., preferably 49-59° C., and more preferably 55-59° C. Suitable primers for quantifying levels of certain precursor miRNAs in test samples obtained from human subjects include, but are not limited to, the primers shown in Table 1.

In one example, the method uses gene-specific primers and a thermostable reverse transcriptase to convert the hairpin of the miRNA precursors to cDNA. The cDNA is subsequently amplified using real-time PCR with SYBR® green detection.

Amplification reactions such as PCR, RT-PCR and real-time PCR are well known in the art. Briefly, in PCR, two primer sequences are prepared which are complementary to regions on opposite complementary strands of, for example, a target nucleic acid. An excess of deoxynucleoside triphosphates (dNTPs) are added to a reaction mixture along with a DNA polymerase, e.g., Taq polymerase. If the target sequence is present in a sample, the primers will bind to the target and the polymerase will cause the primers to be extended by adding on nucleotides. Each nucleotide incorporated results in the generation of a molecule of the targeted nucleic acid. By raising and lowering the temperature of the reaction mixture, the extended primers will dissociate from the nucleic acid template to form amplification products, excess primers will bind to the targeted nucleic acid and to the amplification products and the process is repeated.

Although amplification and analysis of the PCR products can be performed sequentially, in "real-time" PCR assays, amplification and analysis occur simultaneously. DNA dyes or fluorescent probes can be added to the PCR mixture before amplification and used to analyze PCR products during amplification. Sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. See, for example, U.S. Pat. No. 6,174,670, incorporated herein by reference.

The differences in various real-time PCR protocols rests in methods for generating a fluorescence signal with the amplification product. Many different probes are available for monitoring PCR. Although not sequence specific, double stranded DNA (dsDNA) specific dyes can be used in any amplification without the need for probe synthesis. Such dyes include ethidium bromide and SYBR® Green I. With dsDNA dyes, product specificity can be increased by analysis of melting curves or by acquiring fluorescence at a high temperature where nonspecific products have melted. See, for example, Ririe K M, Rasmussen R P and C T Wittwer, Product differentiation by analysis of DNA melting curves during the polymerase chain reaction, Anal. Biochem. 245-154-160 (1997); Morrison T B, J&J Weis and C T Wittwer, Quantification of low copy transcripts by continuous SYBR® Green I monitoring during amplification, BioTechniques 24:954-962 (1998).

Oligonucleotide probes can also be covalently labeled with fluorescent molecules. For example, hairpin probes (Molecular Beacons®) and exonuclease probes (TaqMan®) are dual-labeled oligonucleotides that can be monitored during PCR. Another example is the TaqMan® minor groove binder probe. These probes depend on fluorescence quenching of a fluorophore by a quencher on the same oligonucleotide. Fluorescence increases when hybridization or exonuclease hydrolysis occurs.

Molecular beacons have a hairpin structure wherein the quencher dye and reporter dye are in intimate contact with each other at the end of the stem of the hairpin. Upon hybridization with a complementary sequence, the loop of the hairpin structure becomes double stranded and forces the quencher and reporter dye apart, thus generating a fluorescent signal. Tyagi et al. reported use of the non-fluorescent quencher dyes including the dabcyl (4-{[4-(dimethylamino)phenyl]diazenyl}benzoyl moiety, absorbance max=453 nm) used in combination with fluorescent reporter dyes of widely varying emission wavelength (475-615 nm). See Tyagi S, Bratu D P, Kramer F R, Multicolor molecular beacons for allele discrimination, Nat. Biotechnol. 1:49-53 (1998).

Another format for "real-time" PCR uses DNA probes which are referred to as "5'-nuclease" (or TaqMan®) probes (Lee et al., Nucl. Acid Res. 21:3761-3766 (1993)). These fluorogenic probes are typically prepared with the quencher at the 3' terminus of a single DNA strand and the fluorophore at the 5' terminus. During each PCR cycle, the 5'-nuclease activity of Taq DNA polymerase cleaves the DNA strand, thereby separating the fluorophore from the quencher and releasing the fluorescent signal. The 5'-nuclease assay requires that the probe be hybridized to the template strand during the primer extension step (60-65° C.). It is also possible to effect simultaneous "real-time" detection of more than one polynucleotide sequence in the same assay, using more than one fluorophore/quencher pair.

The TaqMan® minor groove binder (MGB) assay utilizes a hydrolysis probe that has a fluorophore on one end of the probe. The fluorophore may be one of the following chemicals: TAMRA, TET, JOE, VIC or NED. The other end of the probe has the TaqMan® minor groove binder/quencher. The hydrolysis probe (TaqMan® MGB) assay takes advantage of the 5'-nuclease ability of DNA polymerase to hydrolyze the fluorophore and minor groove binder from the probe to produce a signal. The hydrolysis probe methods offer an additional degree of specificity. Methods of preparing such probes are described in U.S. Pat. Nos. 5,801,155; 6,790,945; 6,699,975, and 6,653,473, all of which are incorporated herein in their entirety. The use of the TaqMan® minor groove binder probe is especially appealing in the present invention because the presence of the minor groove binder increases the Tm of the probes and allows for the design of shorter probes that are beneficial for the detection of miRNA precursors since there is only a small region in between the sense and antisense primer.

In real-time PCR, reagents generate a fluorescence signal proportional to the number of amplicons produced by the PCR process. Real-time PCR is based upon the principle that, the more template initially present, the fewer number of cycles are necessary to reach exponential phase where the fluorescence signal rises above the background signal. This point, called the threshold cycle ($C_T$), occurs during the exponential phase and is proportional to the initial template concentration. Thus a standard curve can be generated with gene copy numbers as a function of the threshold cycle to permit quantification of unknown samples without any post-amplification sample processing.

In "real-time quantitative" PCR, the accumulation of amplification products is measured continuously in both standard dilutions of target RNA and samples containing unknown amounts of target RNA. A standard curve is constructed by correlating initial template concentration in the standard samples with the number of PCR cycles (Ct) necessary to produce a specific threshold concentration of product. In the test samples, target PCR product accumulation is measured after the same $C_T$, which allows interpolation of target DNA concentration from the standard curve. Another method, often referred to as "relative quantitative PCR," determines the relative concentrations of specific nucleic acids.

In one example of the present invention, a real-time quantitative PCR assay is used to monitor the expression of miRNA precursors. The method comprises amplifying the targeted hairpin sequence of the miRNA precursor species through a plurality of amplification cycles in the presence of the fluorescent entity, measuring fluorescence intensity of the fluorescent entity at each of the plurality of amplification cycles to produce a fluorescent value for each cycle related to the quantity of the miRNA precursor species present at each cycle, obtaining a score from each of a plurality of tests, each of the plurality of tests using the fluorescence values to generate the score, and using the scores to ascertain whether the miRNA precursor species is present in the sample and to quantity the miRNA precursor in the test sample. The levels of the miRNA precursor species can be quantified in comparison with an internal standard, for example, levels of a synthetic miRNA precursor of the identical sequence. As described above, the methods for quantitative PCR and variations thereof are well known to those of ordinary skill in the art.

Figure 5:
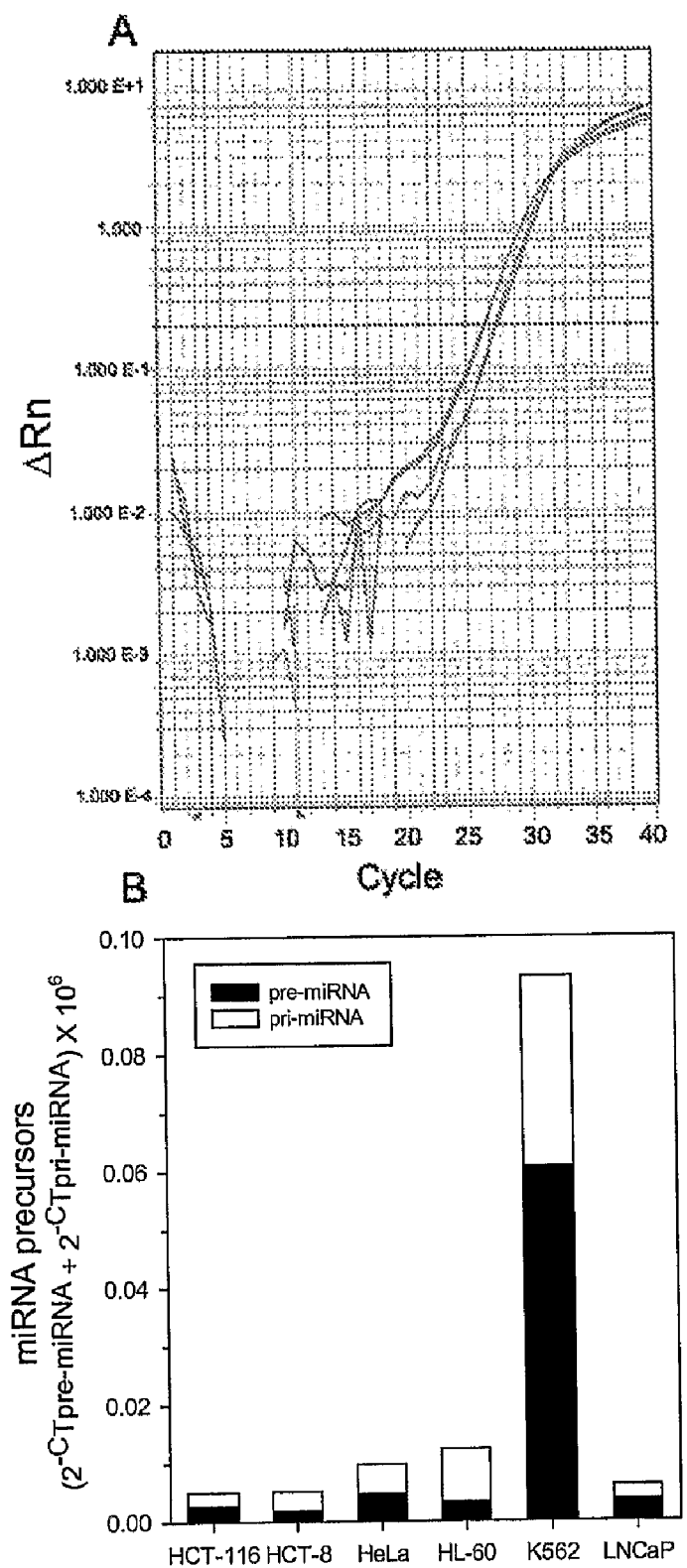
FIG. 5. Pri-miRNA and pre-miRNA expression in human cancer cell lines. (A) Total RNA from HeLa cells was converted to cDNA using gene specific primers as described in Materials and Methods. The cDNA was amplified by real-time PCR using primers that anneal to the hairpin present in both the pri-miR-18 and pre-miR-18 ($C_T$=26.6) or to the pri-miRNA only ($C_T$=27.6). (B) Total miR-18 precursor expression (pri-miRNA+pre-miRNA) and individual expression (pri-miRNA or pre-miRNA) in six cancer cell lines. Mean of duplicate real-time PCRs from a single cDNA sample.

In another example, real-time PCR is used to determine the amount of pre-miRNA precursors only. This method uses a second set of primers, e.g. the reverse primer to the hairpin structure (black primer, FIG. 1) and a new forward primer designed to anneal to a sequence upstream of the hairpin sequence (dashed primer, FIG. 1). In this method, PCR using the hairpin primers (gray/black, FIG. 1) amplifies the pri-miRNA+pre-miRNA, and PCR using the upstream primer along with the reverse hairpin primer (dashed/black, FIG. 1) amplifies only the pri-miRNA. The amount of pre-miRNA is then calculated using the following equation: pre-miRNA= $2^{-C_T\ (pri-miRNA+pre-miRNA)} - 2^{-C_T\ pri-miRNA}$. (FIG. 5).

Figure 13:
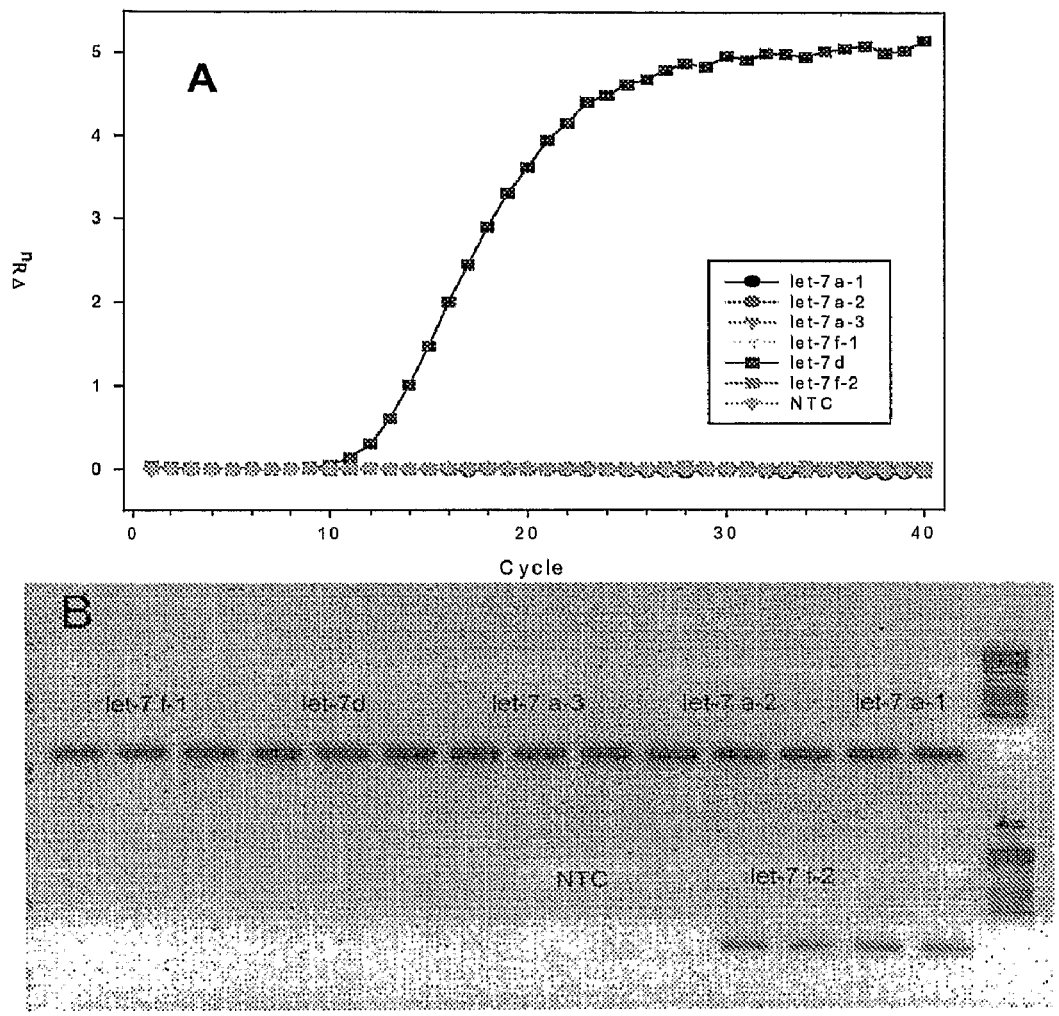
FIG. 13. Real-time PCR of miRNA precursor isoforms. The sequences of six miRNA precursor isoforms (let-7a-1, let-7a-2, let-7a-3, let-7f-1, let-7f-2 and let-7d) were cloned into plasmids. Real-time PCR was attempted on seven different reactions (in triplicate) containing each plasmid and primers specific to each isoform. Each reaction contained the TaqMan® MGB probe for let-7d. Only the reaction containing the let-7d plasmid gave a detectable signal (A). Following the real-time PCR, a portion of each reaction was run on an agarose gel to demonstrate that PCR had occurred in each reaction (B). NTC, No template control. M, 100 bp DNA ladder.

In another example, TaqMan® minor groove binder probes are used to discriminate nearly identical members of a family of miRNA isoforms. (FIGS. 12, 13)

In another example, the assay is adapted and expanded to include primers to some 200 human miRNA precursors. (FIG. 15). In this example, miRNA precursor expression is profiled in 32 human cell lines from lung, breast, colorectal, hematologic, prostate, pancreatic and head and neck cancers.

The invention may also comprise one or more kits to perform any of the methods described herein. In one embodiment the kit comprises one or more primer pairs that target the hairpin region of one or more precursor miRNAs. In another embodiment, the kit may further comprise a hairpin specific primer and/or a gene specific primer that targets a region in the primary miRNA that is substantially upstream or downstream of the hairpin sequence. In another embodiment, the kit may comprise, alone or in combination with other regents, a gene-specific reverse primer to a sequence within the hairpin structure to be used to reverse transcribe the hairpin sequence of miRNA precursor to cDNA. In a non-limiting example, primers, enzymes for reverse transcription, and enzymes for amplification may be included in the kit. The kits may also comprise agents for RNA isolation, purification of amplification products, labels, etc.

The components of the kits may be packaged either in aqueous media or in lyophilized form. The suitable container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention may also include a means for containing the reagent containers in close confinement for commercial sale. Such containers may include injection or blow-molded plastic containers into which the desired vials are retained.

While the present teachings have been described in terms of the following examples, those skilled in the art will readily understand that numerous variations and modifications of these examples are possible without undue experimentation. All such variations and modifications are within the scope of the current teachings. Aspects of the present teachings may be further understood in light of the following examples, which should not be construed as limiting the scope of the claims in any way.

EXAMPLE 1

Quantification of miRNA Precursors in Human Cancer Cell Lines

Materials and Methods

Cell lines and tissue culture. The following human tumor cell lines were obtained from American Type Culture Collection (Manassas, Va.). K-562 (chronic myelogenous leukemia), HL-60 (promyelocytic leukemia), LNCaP (prostate cancer), HeLa (cervical adenocarcinoma), HCT-8 (colorectal cancer) and HCT-116 (colorectal cancer). S2 Drosophila cells were purchased from Invitrogen (Carlsbad, Calif.). All cancer cell lines were cultured in a humidified atmosphere of 95% air, 5% $CO_2$ using RPMI 1640 or other suitable media and 10% fetal bovine serum. S2 cells were cultured at room temperature according to Invitrogen's protocol.

RNA, DNA extraction and reverse transcription. Total RNA was extracted from the cultured cells using TRIZOL (Invitrogen, Carlsbad, Calif.) per the manufacturer's protocol. The concentration of total RNA was quantified by the absorbance at 260 nm. Total RNA was briefly exposed to RNAase-free DNAase I as previously described by Calin, G. A., et al., Frequent deletions and down-regulation of micro-RNA genes miR15 and miR16 at 13q14 in chronic lymphocytic leukemia. Proc Natl Acad Sci USA, 2002. 99(24): p. 15524-9. RNA was reverse transcribed to cDNA using either random hexamers or gene specific primers and Thermoscript, thermostable reverse transcriptase (Invitrogen). A 1 µg aliquote of DNase treated total RNA (10.5 µl total volume) was incubated with 1.5 µl of a cocktail containing 10 µM of each of the antisense primers listed in Table 1. The reaction was heated to 80° C. for 5 min to denature the RNA, then incubated for 5 min at 60° C. to anneal the primers. The reactions were cooled to room temperature and the remaining reagents (5× buffer, dNTPs, DTT, RNase inhibitor, Thermoscript) were added as specified in the Thermoscript protocol and the reaction proceeded for 45 min at 60° C. Finally, the reverse transcriptase was inactivated by a 5 min incubation at 85° C. For the random hexamer primed cDNA, RNA plus 0.25 µl of random primers (Invitrogen) was denatured at 80° C. for 5 min and cooled to room temperature for 10 min to allow the hexamers to anneal. The additional reagents were then added and the reaction proceeded as described above. The minus reverse transcription controls were treated identically as described above except the reactions lacked Thermoscript and primers. Genomic DNA was isolated from HeLa cells as previously described in Sharma, R. C., A. J. Murphy, M. G. DeWald, and R. T. Schimke, A rapid procedure for isolation of RNA-free genomic DNA from mammalian cells. Biotechniques, 1993. 14(2): p. 176-8.

Gene expression in Low Molecular Weight RNA fraction. Total RNA was isolated from HCT-116 cells using Trizol. Seven hundred μg of total RNA was loaded to the Midi RNA isolation column (Qiagen, Valencia, Calif.). Isolation of low molecular weight (LMW) RNA (approximately 160 nt and less) was achieved following the manufacturer's protocol, including eluting the LMW RNA using buffer QRW2 (750 mM NaCl, 50 mM MOPS, pH 7.0, 15% (v/v) ethanol). Total and LMW RNA were resolved on a denaturing 15% polyacrylamide gel to validate the isolation. One μg of the LMW and total RNA was reverse transcribed to cDNA using Thermoscript and random hexamers or gene specific primers as described above. The cDNA was assayed by real-time PCR using primers for six different miRNA genes and U6 RNA.

Northern Blotting. Northern blotting was performed as previously reported in Lau, N. C., et al., An abundant class of tiny RNAs with probable regulatory roles in *Caenorhabditis elegans*. Science, 2001. 294(5543): p. 858-62. Briefly, total RNA (30 μg) was resolved on 15% polyacrylamide urea gels and transferred to Genescreen Plus membranes (Perkin Elmer, Boston, Mass.). Oligonucleotides complementary to the mature miRNA were end-labeled with [γ $^{32}$P] ATP and T4 kinase. The membranes were incubated with labeled probe (1.5×10$^6$ c.p.m./ml hybridization buffer) prior to visualization using phosphorimaging. Blots were stripped once and re-probed using an oligonucleotide complementary to U6 RNA.

Primer design, PCR and validation. All primers were designed using Primer Express version 2.0 (Applied Biosystems, Foster City, Calif.). The following criteria were used during the primer design. Both sense and antisense primers were designed to be located within the hairpin sequence of the miRNA precursors (FIG. 1). The pre-miRNA sequences are predicted based upon the fold-back structure (described in Griffiths-Jones, S., The microRNA Registry. Nucleic Acids Res, 2004. 32(1): p. D109-11; and Ambros, V., et al., A uniform system for microRNA annotation. Rna, 2003. 9(3): p. 277-279). Mapping the 5' and 3' cleavage sites of miR-30a demonstrated that the termini of pre-miR-30a are identical to those of mature 30a and 30a* (see Lee, Y., et al., The nuclear RNase III Drosha initiates microRNA processing. Nature, 2003. 425(6956): p. 415-9). It was presumed here that all pre-miRNAs are processed from the pri-miRNA in this manner. A maximal extension of about 4 nt was allowed for each primer over the presumed 5' or 3' termini of the pre-miRNA. Since the hairpin is contained within both the pri-miRNA and the pre-miRNA, primers designed to the hairpin simultaneously amplify both RNAs. We use the term 'miRNA precursors' here to be inclusive of both the pri-miRNA and the pre-miRNA. Primers were designed with a maximal $T_m$ difference between both primers of ≦2° C. and a primer length between 18-24 nts. An ideal Tm of 55-59° C. was selected for the primers, however due to size constraints, some primers were designed with a $T_m$ that was below 55° C. The $T_m$ range of all the pre-miRNA primers was 49-59° C., and the median Tm was 56° C. (Table 3). Additional criteria included no 3' GC clamps, and a minimal amplicon size of about 55 bp.

PCR amplicons were validated using gel electrophoresis (2.2% agarose or 15% polyacrylamide) and by the presence of one peak on the thermal dissociation curve generated by the thermal denaturing protocol that followed each real-time PCR run (see Schmittgen, T. D., et al., Quantitative reverse transcription-polymerase chain reaction to study mRNA decay: comparison of endpoint and real-time methods. Anal Biochem, 2000. 285(2): p. 194-204). The sequences of the miRNA precursor amplicons were determined by subcloning the PCR product generated by amplifying HeLa cell cDNA into TOPO TA cloning vectors (Invitrogen) per the manufacturer's protocol. Plasmid purification and automated DNA sequencing of the plasmids were performed using standard techniques.

TABLE 1

PCR Primers used to amplify human miRNAs precursors.

| Gene | Forward primer (5'->3') | Reverse primer (5'->3') | Tm primers (Forward/Rev) |
|---|---|---|---|
| U6 | CTCGCTTCGGCAGCACA (SEQ ID NO: 22) | AACGCTTCACGAATTTGCGT (SEQ ID NO: 23) | 59/59 |
| let-7d | AACGCTTCACGAATTTGCGT (SEQ ID NO: 23) | AAGGCAGCAGGTCGTATAGT (SEQ ID NO: 437) | 55/53 |
| miR-15a | GTAGCAGCACATAATGGTTTGTG (SEQ ID NO: 460) | GCAGCACAATATGGCCTG (SEQ ID NO: 43) | 56/55 |
| miR-16 | GCAGCACGTAAATATTGGCGT (SEQ ID NO: 46) | CAGCAGCACAGTTAAATACTGGAG (SEQ ID NO: 461) | 59/57 |
| miR-18 | TAAGGTGCATCTAGTGCAGATAG (SEQ ID NO: 52) | GAAGGAGCACTTAGGGCAGT (SEQ ID NO: 53) | 53/55 |
| miR-20 | GCACTAAAGTGCTTATAGTGCAG (SEQ ID NO: 60) | GTACTTTAAGTGCTCATAATGCA (SEQ ID NO: 61) | 53/51 |
| miR-21 | GCTTATCAGACTGATGTTGACTG (SEQ ID NO: 62) | CAGCCCATCGACTGGTG (SEQ ID NO: 63) | 53/55 |
| miR-24-2 | CTCCCGTGCCTACTGAGCT (SEQ ID NO: 70) | CCCTGTTCCTGCTGAACTGAG (SEQ ID NO: 71) | 57/59 |

TABLE 1-continued

PCR Primers used to amplify human miRNAs precursors.

| Gene | Forward primer (5'->3') | Reverse primer (5'->3') | Tm primers (Forward/Rev) |
|---|---|---|---|
| miR-28 | GGAGCTCACAGTCTATTGAGTTACC (SEQ ID NO: 80) | CCTCCAGGAGCTCACAATCT (SEQ ID NO: 81) | 56/56 |
| miR-29 | ATGACTGATTTCTTTTGGTGT (SEQ ID NO: 82) | ATAACCGATTTCAGATGGTG (SEQ ID NO: 83) | 49/51 |
| miR-30a | GTAAACATCCTCGACTGGAAGCT (SEQ ID NO: 86) | GCTGCAAACATCCGACTGAA (SEQ ID NO: 87) | 58/58 |
| miR-30d | GTTGTTGTAAACATCCCCGAC (SEQ ID NO: 102) | GCAGCAAACATCTGACTGAAAG (SEQ ID NO: 103) | 56/56 |
| miR-33 | TGTGGTGCATTGTAGTTGCA (SEQ ID NO: 110) | CTGTGATGCACTGTGGAAAC (SEQ ID NO: 111) | 56/54 |
| miR-92-1 | TCTACACAGGTTGGGATCGG (SEQ ID NO: 118) | CGGGACAAGTGCAATACCATA (SEQ ID NO: 119) | 57/57 |
| miR-93-1 | AAGTGCTGTTCGTGCAGG (SEQ ID NO: 122) | CTCGGGAAGTGCTAGCTCA (SEQ ID NO: 123) | 55/55 |
| miR-101 | GCCCTGGCTCAGTTATC ACA (SEQ ID NO: 136) | GCCATCCTTCAGTTATCACAGTA (SEQ ID NO: 137) | 57/55 |
| miR-105-1 | CAAATGCTCAGACTCCTGTGGT (SEQ ID NO: 142) | GCACATGCTCAAACATCCGT (SEQ ID NO: 143) | 58/58 |
| miR-107 | CAGCTTCTTTACAGTGTTGCCT (SEQ ID NO: 148) | GATAGCCCTGTACAATGCTGC (SEQ ID NO: 149) | 56/56 |
| miR-124a- | TCCGTGTTCACAGCGGAC (SEQ ID NO: 154) | CATTGACCGCGTGCCTTA (SEQ ID NO: 155) | 58/58 |
| miR-147 | CTAAAGACAACATTTCTGCAGAC (SEQ ID NO: 210) | TCTAGCAGAAGCATTTCCAC (SEQ ID NO: 211) | 53/53 |
| miR-216 | TGGCTTAATCTCAGCTGGCA (SEQ ID NO: 304) | TGAGGGCTAGGAAATTGCTGT (SEQ ID NO: 305) | 58/58 |
| miR-219 | TCCTGATTGTCCAAACGCAA (SEQ ID NO: 310) | GGGACGTCCAGACTCAACTCTC (SEQ ID NO: 311) | 59/59 |
| miR-220 | CCACACCGTATCTGACACTTT (SEQ ID NO: 312) | CAGACCGCATCATGAACAC (SEQ ID NO: 313) | 54/54 |
| miR-224 | GGCTTTCAAGTCACTAGTGGTTC (SEQ ID NO: 320) | CTTTGTAGTCACTAGGGCACCA (SEQ ID NO: 321) | 56/56 |

Real-time quantitative PCR. Real-time quantitative PCR was performed using standard protocols on an Applied Biosystem's 7900HT Sequence Detection System. Briefly 5 µl of a 1/100 dilution of cDNA in water was added to 12.5 µl of the 2× SYBR® green PCR master mix (Applied Biosystems), 800 nM of each primer and water to 25 µl. The reactions were amplified for 15 sec at 95° C. and 1 min at 60° C. for 40 cycles. The thermal denaturation protocol was run at the end of the PCR to determine the number of products that were present in the reaction. All reactions were run in triplicate and included no template and no reverse transcription controls for each gene. The cycle number at which the reaction crossed an arbitrarily-placed threshold ($C_T$) was determined for each gene and the relative amount of each miRNA to U6 RNA was described using the equation $2^{-\Delta C_T}$ where $\Delta C_T = (C_{TmiRNA} - C_{TU6RNA})$ (See Livak, K. J. and T. D. Schmittgen, Analysis of relative gene expression data using real-time quantitative PCR and the 2(−Delta Delta C(T)) Method. Methods, 2001. 25(4): p. 402-8.) Relative gene expression was multiplied by $10^6$ in order to simplify the presentation of the data.

Calculation of PCR efficiency. PCR efficiency was determined as previously described in Mygind, T., et al., Determination of PCR efficiency in chelex-100 purified clinical samples and comparison of real-time quantitative PCR and conventional PCR for detection of *Chlamydia pneumoniae*. BMC Microbiol, 2002. 2(1): p. 17, from the equation $N = N_0 \times E^n$, where N is the number of amplified molecules, $N_0$ is the initial number of molecules, n is the number of PCR cycles and E is the efficiency, which is ideally 2. When the equation is of the form $n = -(1/\log E) \times \log N_0 + (\log N/\log E)$, a plot of log copy number versus $C_T$ yields a straight line with a slope = $-(1/\log E)$. To experimentally determine PCR efficiency, 10-fold dilutions of HeLa cell genomic DNA were diluted over 4-logs. The diluted genomic DNA was amplified by real-time PCR using the identical conditions established for the gene expression analysis. Plots were made of the log of the template concentration versus the $C_T$ and the PCR efficiency was calculated from the slope of the line using the equation described above. Actual concentration of template is not needed when determining the efficiency as it depends only upon the slope of the line.

Treeview Analysis of PCR data. The expression of each miRNA relative to U6 RNA was converted to pseudocolors and plotted using the Treeview cluster analysis as previously reported in Dittmer, D. P., Transcription Profile of Kaposi's Sarcoma-associated Herpesvirus in Primary Kaposi's Sarcoma Lesions as Determined by Real-Time PCR Arrays. Cancer Res, 2003. 63(9): p. 2010-5; Fakhari, F. D. and D. P. Dittmer, Charting latency transcripts in Kaposi's sarcoma-associated herpesvirus by whole-genome real-time quantitative PCR. J Virol, 2002. 76(12): p. 6213-23; Eisen, M. B., et al., Cluster analysis and display of genome-wide expression patterns. Proc Natl Acad Sci USA, 1998. 95(25): p. 14863-8). Expression that had a value equal to 1 was designated black, expression that was greater than 1 was designated red and expression that was less than one was designated as green. Genes with undetectable expression were designated as gray.

Results

Figure 2:
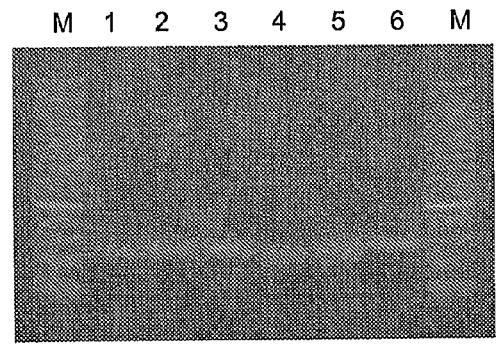
FIG. 2. Amplification of short hairpins by the PCR. HeLa cell genomic DNA was amplified by the PCR using primers for miR-124a-2 (lane 1), miR-93-1 (lane 2), let7-d (lane 3), miR-15a (lane 4), miR-16 (lane 5) and miR-147 (lane 6) and resolved on a 2.2% agarose gel. M, 25 bp DNA ladder.

Validation of PCR primers. To amplify the miRNA precursors, PCR primers were designed to anneal to the hairpin (FIG. 1). Amplification of short hairpins by the PCR could present a challenge because of the competition between annealing of the primer and reformation of the hairpin. Primers were designed to 23 different pre-miRNA genes using the criteria described in Materials and Methods. Shown in FIG. 2 are the products from amplifying HeLa cell genomic DNA using six of the miRNA precursor primers. All six reactions produced amplicons of the expected size with no additional products. All of the primer pairs listed in Table 3 met the criteria of one peak on the thermal dissociation curve and a single band of the correct size on either agarose or polyacrylamide gels. As a further validation, the amplicon from pre-miR-147 was subcloned and sequenced. Comparison of the sequence data verified that 100% of the new sequence was amplified. These results demonstrate our ability to successfully amplify short hairpins using the PCR.

Validation of reverse transcription conditions. Our initial attempts to reverse transcribe total RNA used random hexamer priming. Real-time PCR of the resulting cDNA using the primers listed in Table 1 produced varied PCR signals in the cell lines tested, i.e., miRNA precursors were expressed at high, intermediate and low levels (data not shown). It later occurred to us that it may be very difficult to prime the pre-miRNA with random hexamers. This is because pre-miRNAs are very short (<80 nt) and the stoichiometry of primer annealing should be much less than that of a primer binding to a larger RNA such as mRNA. Furthermore, a competition exists between the annealing of the random primers to the pre-miRNA and hairpin formation, which is compounded by the low temperatures (25° C.) at which random primers are typically annealed. We hypothesized that the PCR signal generated from amplifying cDNA primed with random hexamers was due to amplifying the much longer pri-miRNA and not the pre-miRNA.

To test this hypothesis, a LMW RNA fraction was isolated from total RNA. The LMW RNA fraction contains RNA<160 nt and should separate the pre-miRNA (~75 nt) from the larger pri-miRNA. Denaturing polyacrylamide gel electrophoresis verified that RNA<160 nt was recovered in the LMW fraction (not shown). Both the LMW and total RNA was primed with random hexamers or gene specific primers and reverse transcribed using the Thermoscript reverse transcriptase.

Figure 3:
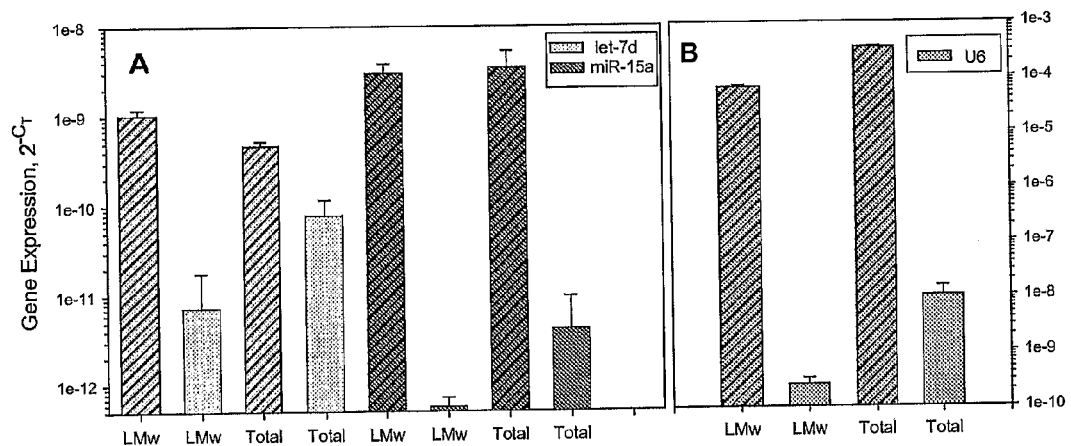
FIG. 3. Optimal reverse transcription conditions for small RNAs. Total RNA was isolated from HCT-116 cells, a fraction of which was further purified to contain a low molecular weight (LMW) fraction of <160 nt. One µg of total or LMW RNA was converted to cDNA using Thermoscript reverse transcriptase and random hexamers (open bars) or gene specific primers (stripped bars). The resulting cDNA was amplified by real-time PCR using primers for (A) let7d, miR-15a or (B) U6 RNA. Mean±SD, triplicate PCRs from a single cDNA.

In order to determine the effectiveness of priming the reverse transcriptions, real-time PCR was performed on the cDNA using primers for two miRNAs (let7d and miR-15a) as well as U6 RNA. Total RNA primed with random hexamers produced less cDNA compared to total RNA primed with gene specific primers (FIG. 3). More LMW RNA was converted to cDNA when primed with gene specific primers compared to random hexamers (FIG. 3). Even for the 106 nt U6 RNA that does not contain any hairpins, higher yields of cDNA were achieved using the gene-specific priming compared with random hexamers (FIG. 3B). We conclude that reverse transcription proceeds through secondary structure such as hairpins if priming occurs at some point upstream of the hairpin. However, to prime short RNA molecules, in particular small RNAs containing hairpins, gene-specific primers and not random primers should be used.

Intra-assay variation. To evaluate the intra-assay variation of the real-time PCR assay, flasks of HeLa, HCT-116 and HL-60 cells were cultured in triplicate. Total RNA was isolated from the cultures. A 1 μg aliquot of the total RNA was converted to cDNA as described in Materials and Methods. The relative expression of the precursors for miR-18, -107 and -29 were determined using the real-time PCR assay. The mean, standard deviation and coefficient of variation from the triplicate RNA isolations/reverse transcription are shown in FIG. 10. The coefficient of variation among the different genes and cell lines was quite low, ranging from 1.8 to 34.5%.

Real-time PCR of miRNA precursors. An important issue for quantitative PCR is that the efficiency of amplification for each gene in the study (including the internal control) should be very similar and be close to the ideal value of 2. Although amplicon lengths were very similar and all the miRNA genes contained the hairpin, large differences in the $T_m$ existed among the primers (Table 1). PCR efficiency was determined on the U6 RNA as well as six miRNA genes, two with a low $T_m$ (49-53° C.), two with an intermediate $T_m$ (55-56° C.) and two with a higher $T_m$ (58-59° C.). The efficiency of all seven genes was very similar and was close to the ideal value of 2 (FIG. 11). There was no trend of altered efficiency with $T_m$ in these genes.

The cDNA of K-562, HL-60, LNCaP, HeLa, HCT-8, HCT-116 and Drosophila S2 cells were amplified by the PCR using primers for 23 miRNA precursors. Moderate to strong PCR signals were generated when cDNA was used as a template for most of the miRNA precursor primers. PCR amplicons were not generated from the S2 cDNA, or in the no template or no reverse transcription controls. In the cases where expression of the miRNA genes was very low ($C_T \geq 35$), the primers were validated on HeLa cell genomic DNA. This was done in order to determine if the weak signal generated by amplifying cDNA was due to the primers not working or to the lack of template in the cDNA (i.e. the gene was not expressed).

The reproducibility of real-time PCR tends to become worse when very low copies of template are amplified. For this reason, the following criteria were used to calculate the mean relative gene expression and to distinguish between low and undetectable expression. If three out of three PCRs were above the threshold after 40 cycles and the thermal dissociation profiles of all three reactions matched, the $C_T$ of all three plots was used in the relative expression calculation. If two out of three PCRs were above the threshold after 40 cycles and the thermal dissociation plots of the two reactions matched, then the PCR that was below threshold was discarded and the mean of the remaining two was used in the relative expression calculation. If only one or no PCRs out of three were above threshold after 40 cycles, then the expression of the gene was classified as 'undetectable'.

Figure 4:
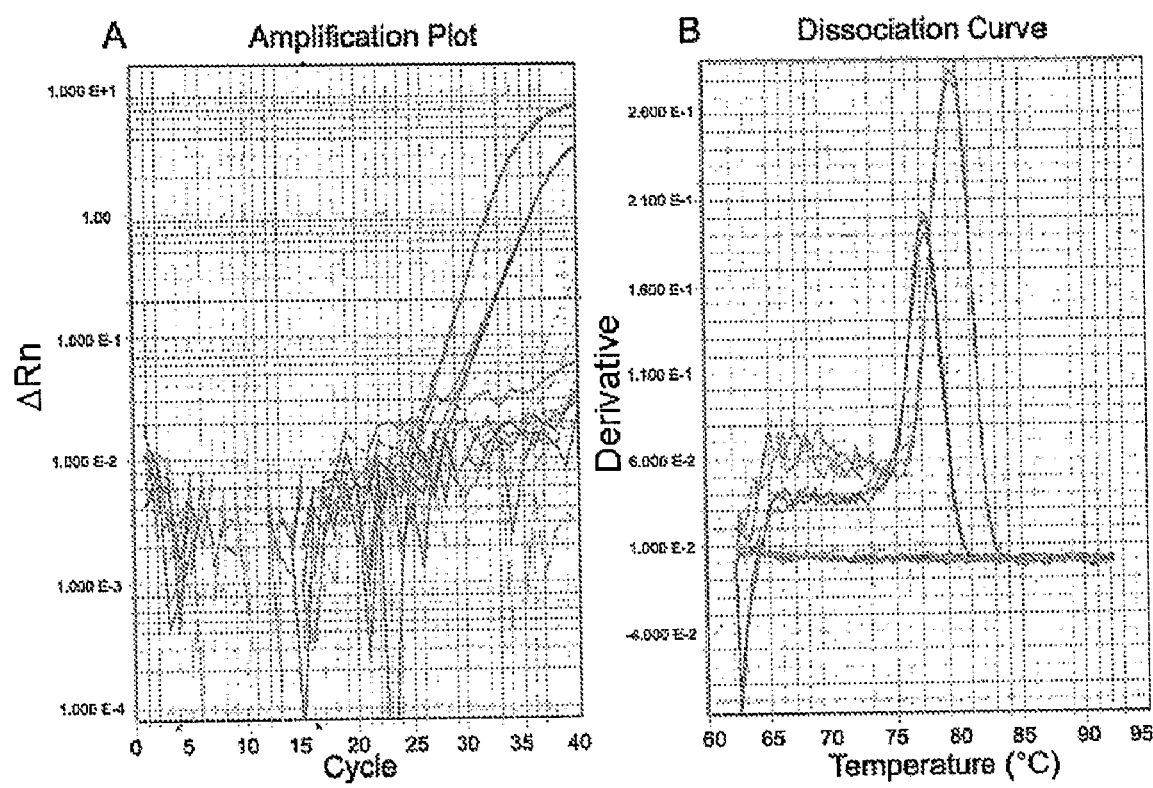
FIG. 4. Real-time PCR of miRNA precursors. Gene specific primers were designed to the hairpin of the miR-21 and let-7d miRNA precursors. The cDNA from human cancer cell lines was amplified by real-time PCR and SYBR® green detection. (A) Real-time, PCR plots of HCT-8 cDNA using miR-21 primers (blue plot, $C_T$=32.8) and let-7d primers (red plot, $C_T$=29.7). Also shown are the signals that were generated from the no template control reactions (olive plots) and the no reverse transcription control reactions purple plots). (B) Dissociation curve generated from the heat dissociation protocol that followed the real-time PCR shown in (A). The presence of one peak on the thermal dissociation plot corresponds to a single amplicon from the PCR. The plot colors in (B) match those described in (A).
Figure 6:
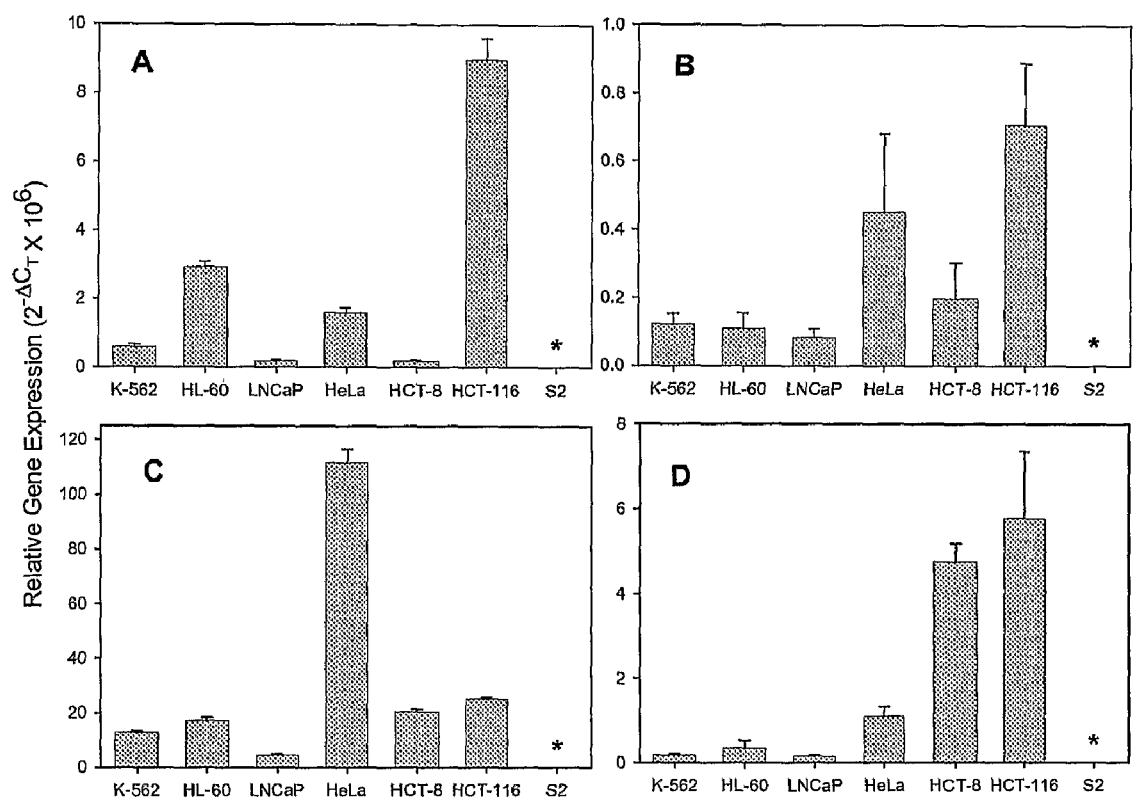
FIG. 6. miRNA precursor expression in human cancer cell lines. The expression of the miRNA precursors for miR-93-1 (A), miR-147 (B), miR-24-2 (C) and miR-29 (D) in six human tumor cell lines and *Drosophila* S2 cells was determined by real-time PCR. Gene expression is presented relative to U6 RNA. Mean±SD of triplicate real-time PCRs from a single cDNA sample. * Undetectable expression.
Figure 7:
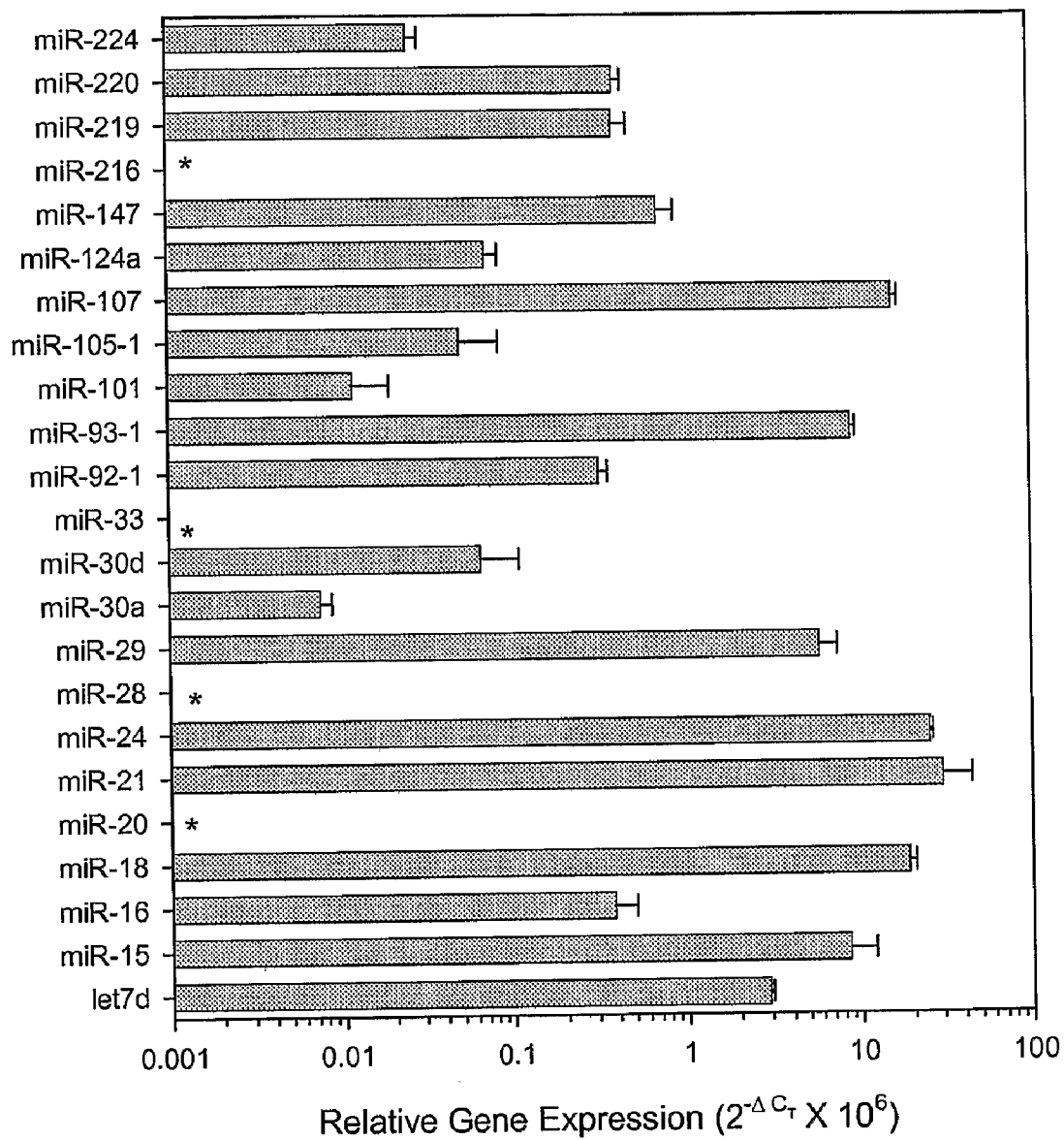
FIG. 7. miRNA precursor expression in the human colorectal cancer cell line HCT-116. The expression of 23 miRNA precursors was determined in the human colorectal cancer cell line HCT-116 by real-time PCR. Gene expression is presented relative to U6 RNA. Mean±SD of triplicate real-time PCRs from a single cDNA sample. * Undetectable expression.

Representative real-time amplification plots of the pre-miRNA are shown in FIG. 4. Shown are the PCR plots for miR-21 and let-7d in HCT-8 cDNA (FIG. 4A). Strong signals were generated for both genes when cDNA template was amplified but not on the no template or no reverse transcription controls. The thermal dissociation curves generated at the end of the real-time PCR run demonstrate that the miR-21 and let-7d primers amplified a single product that was different from the products generated on the negative controls (FIG. 4B). FIG. 4 demonstrates how the dissociation curves may be used to distinguish true PCR amplicons from the noise that is often generated by amplifying no template controls or low copies of template.

miRNA precursor expression in human cancer cell lines. The relative expression of 23 miRNA precursors was determined in six human cancer cells lines. Expression data on four miRNA precursor genes are shown in FIG. 6. The expression of miR-93-1 in the HCT-116 colorectal cancer cell line was 50-fold higher than in the HCT-8 colorectal cancer cell line (FIG. 6A). miR-24-2 was expressed at relatively constant levels in all of the cell lines except in Hela cells which expressed between 5 to 10-fold higher levels (FIG. 6C). The colorectal cancer cell lines and HeLa cells expressed higher levels of miR-29 and miR-147 compared to the blood cancers and prostate cancer cell lines (FIGS. 6B and D). The expression of the 23 miRNA precursors varied within a particular cell type such as HCT-116 (FIG. 7). The difference in expression of the miRNA precursors varied over 4,000-fold within this cell line. miR-21 had the highest level of expression and miR-30a, the lowest level of expression. The expression of four miRNAs (miR-20, -28, -33 and -216) was undetectable expression in HCT-116 cells.

Figure 8:
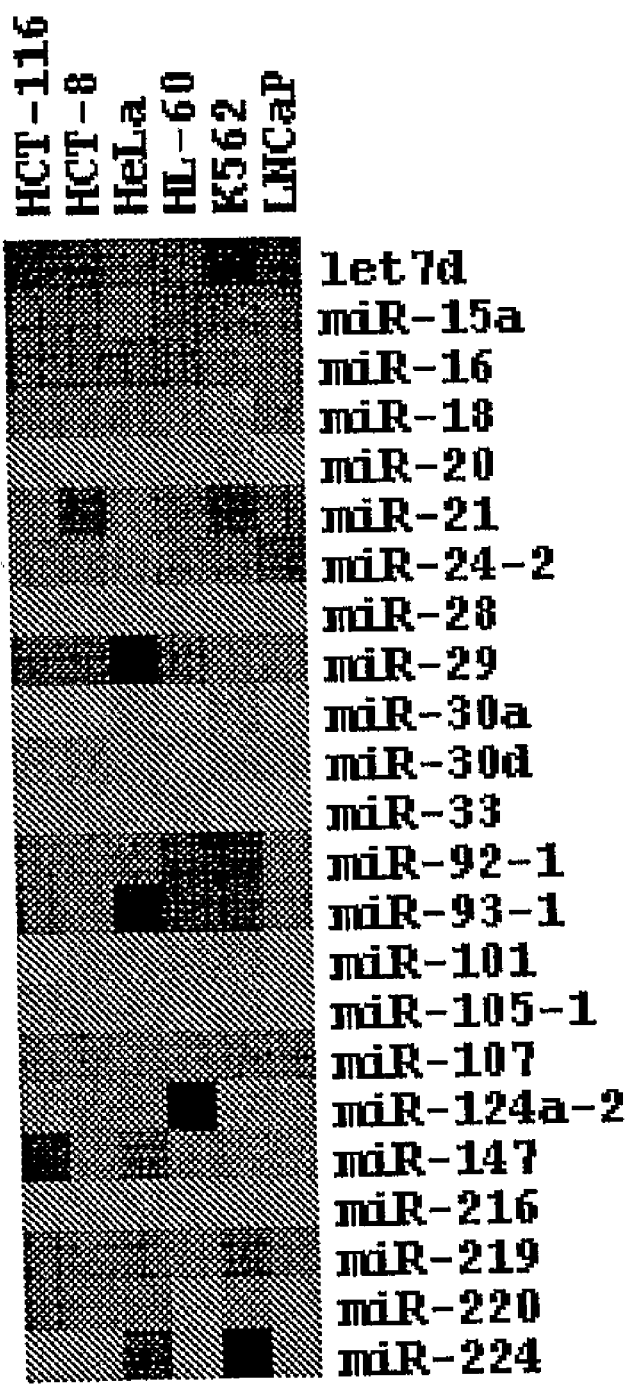
FIG. 8. Treeview analysis of real-time PCR data. The expression of 23 miRNA precursors and U6 RNA was determined in 6 human cancer cell lines by real-time PCR. The relative expression of each gene (mean of triplicate real-time PCRs from a single cDNA sample) was determined as described in Materials and Methods. A median expression value equal to one was designated black. Red shading indicates increased levels of expression and green shading represents decreased levels of expression relative to the median. Gray color, undetectable expression. Data is presented on a logarithmic scale.

The relative expression of the miRNA precursors was presented using the Treeview algorithm (FIG. 8). This allowed visualization of large amounts of data in a single figure. The relative gene expression values were multiplied by $10^6$. Median expression was set equal to the value of one and was indicated by the color black (FIG. 8). Increased (red), decreased (green) and no expression (gray) were plotted relative to the median value. Although some exceptions existed, miRNA precursor expression across the cell lines were more or less similar (i.e. expression was either high, intermediate, low or undetectable in each of the six cell lines). This type of analysis allows for the easy identification of individual genes with very different expression within the group. For example HCT-116 and HeLa cells expressed much higher levels of miR-21 than the other cell lines and miR-224 was undetectable only in HL-60 cells.

Figure 9:
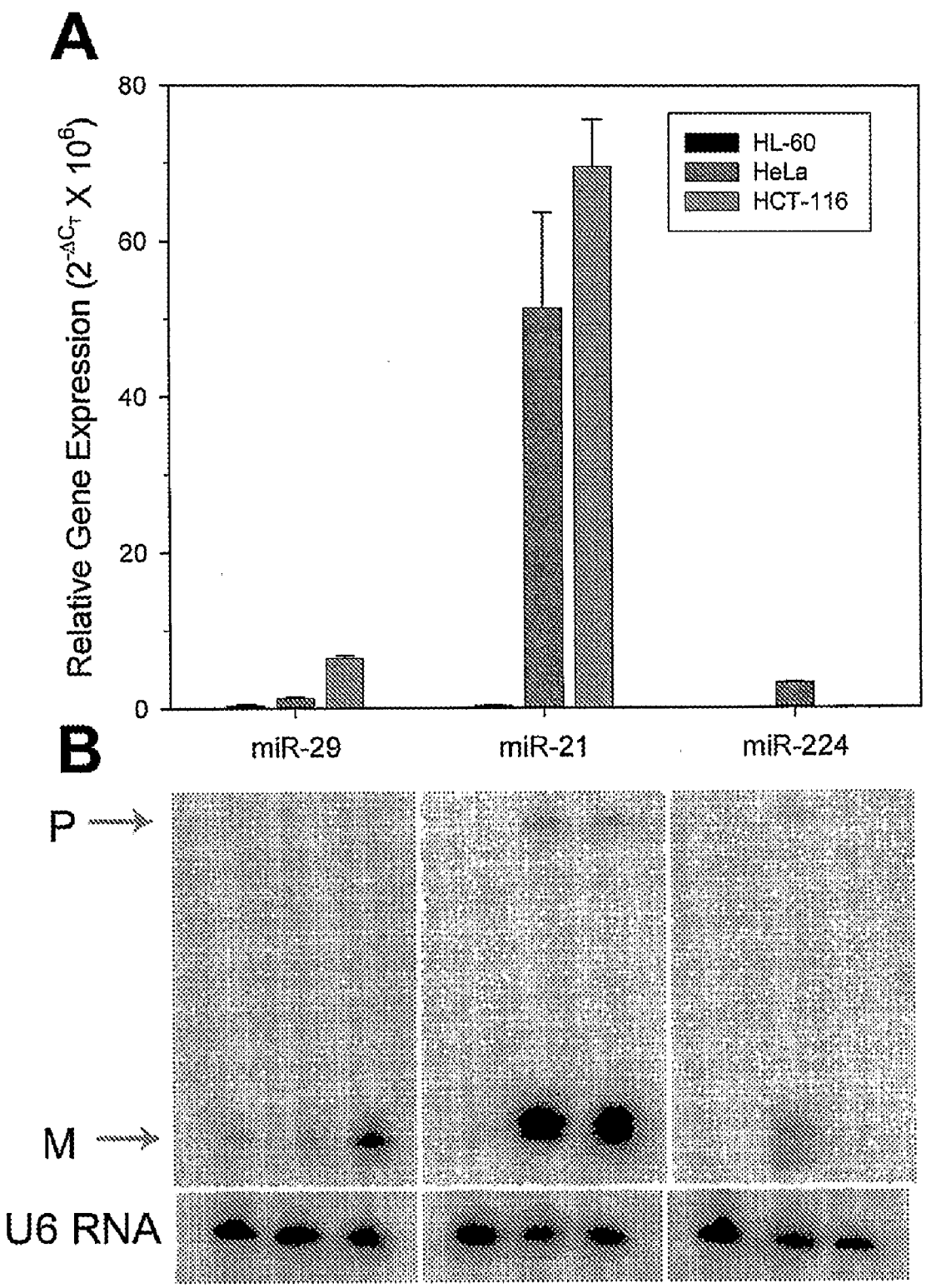
FIG. 9. Validation of real-time PCR data by Northern blotting. (A) The precursor expression for miR-29, -21 and -224 relative to U6 RNA was determined by real-time PCR in HL-60, HeLa and HCT-116 cDNA (mean±SD triplicate RNA isolations/reverse transcriptions). (B) Northern blot of the ~22 nt mature miRNA and the ~75 nt pre-miRNA in the same cell lines shown in (A). The blots were stripped and re-probed for U6 RNA. P, pre-miRNA, M, mature miRNA.

Validation of Real-time PCR results with Northern blotting. Northern blotting is currently the established method to monitor miRNA expression. In order to validate our real-time PCR data, Northern blotting was performed on the total RNA from three different cells lines using probes for miR-29, -21 and -224. miRNAs were selected that demonstrated high expression by our PCR assay and that had diverse expression among the cell lines. The trend in expression between the mature miRNAs as detected by Northern blotting and the miRNA precursors as detected by PCR was identical (FIG. 9). The pre-miRNA was visible by Northern blotting only for miR-21 (HeLa and HCT-116) and miR-224 (HeLa). While strong amplification was generated on miR-29 (HCT-116), no pre-miRNA band was visible by Northern blotting. We were unable to detect any miRNA (mature or precursor) using a probe for miR-220. While Northern blots were attempted using probes for only four miRNAs, the lower limit of detection by Northern blotting was a relative expression value of $0.25 \times 10^6$ by the PCR assay. This suggests that most of the miRNAs labeled as green in FIG. 8 would be undetectable by Northern blotting in our hands and substantiates the enhanced sensitivity of the PCR compared to Northern blotting.

Discussion.

As an alternative to Northern blotting, we developed a real-time PCR assay to quantify the expression of the miRNA precursors. The short hairpins of 23 of 29 genes attempted were successfully converted to cDNA and amplified using standard real-time PCR methods. For this reason we believe that the assay may be expanded to include most of the human miRNA precursors and could eventually include all of the predicted human miRNA genes once discovered. This assay should easily be adaptable to other organisms such as plants, *C. elegans* and *Drosophila*. The Applied Biosystems 7900HT sequence detection system used here was equipped with a 96-well block. This instrument is adaptable to a 384-well block that would increase the assay throughput by 4-fold. Therefore, the assay described here could rival the throughput of microarrays and could be advantageous compared to microarrays due to the increased sensitivity of the PCR. Sensitive PCR assays coupled with methods to capture individual cells such as laser-assisted microdissection can be used to study the cell-type regulation/expression of miRNAs in individual cell types.

Presentation of quantitative PCR data using red/green pseudocolors is a relatively recent phenomena. The only investigator to our knowledge to organize real-time PCR data in such a manner is Dittmer during the development of a genome-wide assay for all of the open reading frames of the Kaposi's sarcoma herpesvirus. It is practical to generate and present gene expression data in this manner only if the number of genes of interest in relatively small (<500). However if the number of genes is relatively small (such as miRNAs) then presentation of real-time PCR data in this manner accomplishes the same result as microarrays, including (i) high throughput analysis of gene expression and (ii) presentation of large amounts of data as pseudocolors to visualize differences in expression levels.

Pre-miRNA is processed to the ~22 nt mature miRNA by Dicer-like enzymes in all species in which miRNAs have been identified. The method described here provides quantitative data on the miRNA precursors only and not on the mature miRNA. Using a transcriptional fusion of the let-7 promoter to gfp, it was shown that let-7 is temporally regulated by transcription and not by processing of the pre-miRNA or stability of the mature miRNA. In CLL patients and cancer cell lines, 23 of 60 samples showed the ~70 nt miR-15a precursor that was not found in any normal tissues except bone marrow. The expression of Dicer was relatively constant in these patients, suggesting inefficient processing of the miRNAs in some CLL patients that was not related to Dicer expression. The precursors of 26 miRNAs were equally expressed in non-cancerous and cancerous colorectal tissue from patients. However, the expression of mature miR-143 and -145 (but not the other 24 miRNAs) was greatly reduced in cancerous tissue compared to non-cancerous tissue, again suggesting altered processing for specific miRNAs in human disease.

We demonstrate here that the expression of three miRNA precursors measured by the PCR assay (miR-21, -29 and -224) paralleled the expression of the mature miRNAs from Northern blots. In order to fully characterize the expression of large numbers of miRNAs, it may be necessary to quantify both the mature and miRNA precursors using sensitive assays such as the PCR. A major challenge in measuring the mature miRNA using RT-PCR is the small size of the mature miRNA (~22 nt). There may be situations (such as in normal development) in which processing or stability of the miRNA is not regulated and the expression of the miRNA precursors reflect the levels of the active, mature miRNA. There may exist other circumstances (such as in human disease), where alterations in miRNA biogenesis produce levels of mature miRNA that are very different than the pre-miRNA. In the former situation, sensitive PCR assays such as the one described here, could be used to measure the miRNA precursor as a means to predict the levels of mature miRNA, while in the latter situation, sensitive assays will be necessary to measure the mature miRNA.

EXAMPLE 2

Quantification of Pre-miRNA

The materials and methods are as described in Example 1. Briefly, PCR using the hairpin primers (FIG. 1) amplifies both the pri-miRNA and pre-miRNA. To amplify only the pri-miRNA, the antisense primer to the hairpin is used along with a new sense primer that is designed to anneal to a sequence upstream of the hairpin sequence of the pri-miRNA (FIG. 1). PCR using the hairpin primers (gray/black, FIG. 1) amplifies the pri-miRNA+pre-miRNA and PCR using the upstream primer along with the antisense hairpin primer (dashed/black, FIG. 1) amplifies only the pri-miRNA. The amount of pre-miRNA is then calculated using the equation:

$$\text{pre-miRNA} = 2^{-C_T(pri\text{-}miRNA+pre\text{-}miRNA)} - 2^{-C_T^{pri\text{-}miRNA}}.$$

Quantification of pri-miRNA and pre-miRNA. All of the miRNA primers were designed to anneal to the hairpin of the miRNA precursors (FIG. 1). A sense primer (5' GGGCTT-TAAAGTGCAGGG 3' (SEQ ID NO: 462)) was designed to the pri-miR-18 (dashed, FIG. 1). This primer along with the antisense primer for miR-18 was used to amplify the pri-miR18. Real-time PCR was performed on the cDNA from the six cancer cell lines using primers for the miR-18 precursors and the pri-miR-18.

The $C_T$ generated from the miR-18 precursors was slightly lower than the $C_T$ for the pri-miR-18 (FIG. 5A). Differences in one $C_T$ unit in real-time PCR data are typical when detecting a 2-fold difference in template. The amount of pre-miRNA was calculated as described in Materials and Methods for Example 1. The relative amounts of pre-miR-18, pri-miR-18 and total precursors (pri-miR-18+pre-miR-18) were determined in each of the six cancer cell lines (FIG. 5B). While more of the miR-18 precursors were expressed in K562 cells, the relative amounts of pri-miR-18 and pre-miR-18 are approximately equal in all six cell lines. This demonstrates that each pri-miRNA is processed to one pre-miRNA molecule and shows that there is no regulation of Drosha processing for miR-18 in these cell lines.

EXAMPLE 3

Use of TaqMan® MGB Probes to Distinguish miRNA Isoforms

Many of the discovered human miRNA genes are grouped in families of two or more nearly identical isoforms. The largest of the human families include let-7 (14 members) and miR-30 (6 members). miRNA isoform families may be one of two types. The first type is when the mature miRNAs have nearly identical sequences, usually differing by 1-3 nt. These families are designated with a letter (e.g. let-7b and let-7c). The second designation is for miRNA genes that produce the identical mature miRNA from a slightly different precursor gene (e.g. let-7a-1 and let-7a-2). These are designated with a number implying that both genes, let-7a-1 and let-7a-2, produce the identical mature miRNA (let-7a). Each isoform is usually located on different chromosomes. There is more sequence diversity in the precursor gene compared to the mature miRNA. For example, while miR-30c-1 and -30c-2 produce the identical mature miRNA, their precursor genes are only 79% identical. The greatest degree of sequence variation on the precursor miRNAs lies in the loop portion of the hairpin.

It is desirable to be able to detect and quantify the expression of only one specific isoform in samples that contain many members of a family of isoforms, e.g. the let-7 family members. To this send, an aspect of the current invention involves designing TaqMan® MGB probes to the loop portion of the miRNA precursor so as to allow discrimination of individual members of a family of miRNA isoforms. The following example illustrates such a method.

Part A of FIG. 12 shows the sequences of 11 members of the human let-7 microRNA family. The red and blue sequences depict the sequences of the forward and reverse primers, respectively for each gene. The sequences colored in yellow differ slightly (primer binding sites only are shown). The sequences in black that lie in between the red and blue primers are the potential sequences to which the TaqMan® probes may be designed to bind to. The purpose of the TaqMan® probe is to allow the PCR product to be detected by the real-time PCR instrument's fluorescent detector. Two things must happen in order for the TaqMan® probes to fluoresce, PCR must occur and the PCR enzyme must cleave the probe. In order for the TaqMan® probes to fluorescence, the probe must bind to 100% of the DNA sequence that lies in between the two primers.

TaqMan® probes are typically designed with a Tm that is 10° C. higher than that of the primers. As shown in FIG. 12, the space in between the primer annealing sites is very short (~15-20 bp). The presence of the MGB allows the design of short TaqMan® probes with Tms ranging from 61-68°.

A TaqMan® MGB probe was designed to anneal to the loop portion of the miRNA precursor. The probe targeted the human let-7d sequence 6FAM—ATT TTG CCC ACA AGG A—MGBNFQ (SEQ ID NO: 467) (double underlined sequence, FIG. 12B). This probe binds to the reverse complementary sequence in the human let-7d gene that lies in between the red and blue primer sequences. Performing PCR on DNA that contains the human let-7d sequence using the gene specific primers for let-7d and the TaqMan® probe fluoresces and will be detectable.

To demonstrate the specificity of detection for the let-7d TaqMan® MGB probe, the sequences of six miRNA isoforms (let-7a-1, let-7a-2, let-7a-3, let-7f-1, let-7f-2 and let-7d) were cloned into plasmids using PCR and TOPO TA cloning. The identity of the sequences was verified by DNA sequencing. Real-time PCR was preformed using gene specific primers to each of the six let-7 isoform plasmids as well as a no template control. The TaqMan® MGB probe for let-7d was included in each of the PCRs. The results show that only the PCR with the let-7d plasmid was detected (FIG. 13A). To demonstrate that amplification of template occurred in each reaction, a sample of each reaction was run on an agarose gel (FIG. 13B). Therefore while amplification occurred in each of the six reactions, only the PCR with the TaqMan® MGB probe detected the amplicon. This demonstrates the specificity of the detection of TaqMan® MGB probes when similar sequences are amplified.

EXAMPLE 4

Expansion of miRNA Precursor PCR Assay

The total number of miRNA precursor assays was expanded to include 201 of the known human miRNAs as of the date of this application. To demonstrate the usefulness of the assay, the expression of 201 miRNAs were screened on samples of RNA from various human tissues (colon, pancreas, ovary, lung and brain). The primers used are presented in FIG. 15 and the results of the analysis is presented in FIG. 14.

Materials and Methods

Cell lines, tissues and tissue culture. The following human tumor cell lines were used: K-562 (chronic myelogenous leukemia), HL-60 (promyelocytic leukemia), Daudi and Ramos (Burkitt lymphoma), Jurkat (T-cell leukemia); LNCaP, PC3, PPC-1, DU145 and TSU-PR1 (prostate); SCC17A, SCC17B, SCCD12, SCC10B and SCC5 (head & neck squamous cell carcinoma); MDA231, T47D, SKBR3, MDA361 and MCF7 (breast cancer); SW620, HCT8, HCT116, HT29 and HCT15 (colorectal carcinoma); Panc1 and Hs 766T (pancreatic); H23, H522, HOP62, A549 and H719 (lung cancer); RH30, RH3, CW9019, SMS-CTR and RD2 (rhabdomyosarcoma) and SK-Hep1, PLC/PRF5, SNU387, SNU449 and H719 (liver cancer). Cells were obtained from American Type Culture Collection (Manassas, Va., USA) or were obtained from various laboratories. Cancer cell lines were cultured in a humidified atmosphere of 95% air, 5% CO2 using RPMI 1640 or other suitable media and 10% fetal bovine serum. Total RNA from normal human liver and skeletal muscle tissue was purchased from Ambion (Austin, Tex.). Hepatocellular carcinoma tumors were received from Dr. Lewis Roberts, Mayo Clinic, Rochester, Minn.

Primers and TaqMan® MGB probes. Primers were designed to all of the known human miRNAs as of December, 2004. These 222 miRNA genes include 38 families of isoforms. Many of the miRNA isoforms differed by only 1-3 bp in the primer binding sequence (FIG. 12). If the difference in sequence occurred towards the 5' end of the primer, then the same pair of primers was used to amplify both isoforms. If the sequence difference occurred towards the 3' end of the primer or there were multiple differences, then a unique pair of primers was designed to each isoform. Although we refer to the expression of 222 miRNA precursors, in actuality, primers were designed to and data are presented on 201 miRNA precursors since several isoforms were amplified by the same pair of primers.

Primers were designed to the primary precursor molecule for several miRNAs. These are designated by the letter "P" in FIG. 15. Primers were designed to the primary precursor if we were unable to successfully design primers to the hairpin-containing precursor. Unsuccessful primer design was defined as either an inability to amplify genomic DNA or detection of multiple products using SYBR® green. The later example could be alleviated using TaqMan® probes. In addition, some primers were designed to the primary precursors of miRNA isoforms. Primers were designed using Primer Express version 2.0 (Applied Biosystems, Foster City, Calif.) using the criteria previously described in EXAMPLE 1. TaqMan® MGB probes were designed using Primer Express software. Probes were designed to have a 5' FAM and a MGB at the 3' end. TaqMan® MGB probes were synthesized by Applied Biosystems. Sequences of the TaqMan® MGB probes are listed in Table 2. Primers were validated on human genomic DNA (Roche), mouse genomic DNA, cDNA synthesized from Universal Human Reference RNA (Stratagene) and no template control reactions.

TABLE 2

TaqMan® MGB probes to members of let-7 family of isoforms.

| Gene | Sequence (5'->3') | Tm (° C.) |
|---|---|---|
| let-7a-1 | 5'-FAM-CACCCACCACTGG-MGB 3' (SEQ ID NO: 463) | 61° |
| let-7a-3 | 5'-FAM-CTCTGCCCTGCTATG-MGB 3' (SEQ ID NO: 464) | 67° |
| let-7b | 5'-FAM-AGTGATGTTGCCCC-MGB 3' (SEQ ID NO: 465) | 65° |
| let-7c | 5'-FAM-AGTTACACCCTGGGA-MGB 3' (SEQ ID NO: 466) | 62° |
| let-7d | 5'-FAM-ATTTTGCCCACAAGGA-MGB 3' (SEQ ID NO: 467) | 67° |
| let-7e | 5'-FAM-ACACCCAAGGAGATC-MGB 3' (SEQ ID NO: 468) | 67° |
| let-7f-1 | 5'-FAM-TTACCCTGTTCAGGAG-MGB 3' (SEQ ID NO: 469) | 63° |
| let-7f-2 | 5'-FAM-TACCCCATCTTGGAG-MGB 3' (SEQ ID NO: 470) | 63° |
| let-7g | 5'-FAM-TACCACCCGGTACAGGA-MGB 3' (SEQ ID NO: 262) | 68° |
| let-7i | 5'-FAM-ATTGCCCGCTGTGGA-MGB 3' (SEQ ID NO: 264) | 67° |

RNA extraction, DNA extraction and reverse transcription. cDNA was synthesized from total RNA using gene specific primers as described in EXAMPLE 1. The gene specific primers included a mixture of each of the antisense primers to all of the miRNAs and U6 RNA listed in the FIG. 15. Following an 80° C. denaturation step and 60° C. annealing, the cDNA was reacted for 45 min at 60° C. as described in EXAMPLE 1. Genomic DNA from NIH 3T3 mouse fibroblasts was isolated as described in Sharma, R. C., et al., A rapid procedure for isolation of RNA-free genomic DNA from mammalian cells. Biotechniques 1993. 14(2):176-8.

Real-time PCR. The expression of the miRNA precursors was determined using real-time quantitative PCR as described in EXAMPLE 1 with several modifications. Three μl of a master mix containing all of the reaction components except the primers was dispensed into a 384-well real-time PCR reaction plate (Applied Biosystems) using a 12-channel repeating pipette (Model EDP3-Plus, Rainin Instruments, Woburn, Mass., USA). The master mix contained 0.5 μl of 10×PCR buffer, 0.7 μl of 25 mM MgCl2, 0.1 μl of 12.5 mM dNTPs, 0.01 μl UNG, 0.025 μl Amplitaq Gold DNA polymerase, 0.5 μl of dilute cDNA (1:50) and water to 3 μl. All of the PCR reagents were from the SYBR® green core reagent kit (Applied Biosystems). A 2 μM solution of each pair of primers listed in FIG. 15 was stored in 12-well PCR strip tubes. Two μl of each primer was dispensed into duplicate wells of the 384-well plate using the 12-channel repeating pipette. Everything was identical for the TaqMan® assays except the TaqMan® core reagent kit (Applied Biosystems) and 200 nM of the TaqMan® MGB primers were used. Each miRNA listed in FIG. 15 and U6 RNA was assayed in duplicate in the 384-well reaction plate. Real-time PCR was performed on an Applied Biosystems 7900HT real-time PCR instrument equipped with a 384-well reaction block. PCR was performed for 15 seconds at 95° and one minute at 60° C. for 40 cycles followed by the thermal denaturation protocol. TaqMan® and SYBR® green assays may be run simultaneously on the 7900HT real-time instrument. The expression of each miRNA relative to U6 RNA was determined using the 2-ΔCT method. To simplify the presentation of the data, the relative expression values were multiplied by 105.

Validation of miRNA precursor primers, SYBR® green. Each pair of primers listed in FIG. 15 was validated on human genomic DNA, cDNA synthesized from Universal Human Reference RNA, mouse genomic DNA and no template control reactions. All of the primers listed in FIG. 15 worked successfully on human genomic DNA (not shown). Successful amplification was defined by the presence of a single dissociation peak on the thermal melting curve. For those reactions that produced multiple dissociation peaks, a new pair of primers were designed to the primary precursor miRNA. These primers are listed with the designation "p", e.g. miR-9-1(p) (FIG. 15). Many of the miRNA genes that required priming of the primary precursor were miRNA genes with known isoforms (e.g. miR-9-1, -19b-1, -106a). About 70% of the human primers successfully amplified mouse genomic DNA (FIG. 15). The ability of primers to amplify both between human and mouse miRNA genes is likely due to the similarity in sequence among these genes. Human miRNA primers were not tested on mouse cDNA.

miRNA precursor expression profiling in cancer cell lines. The expression of 222 miRNA precursors was profiled in 32 commonly used cell lines of lung, breast, head & neck, colorectal, prostate, pancreatic and hematopoietic cancers. Gene expression data was normalized to U6 RNA. U6 was validated as an internal control by comparing its expression levels in each of the cell lines. U6 RNA was consistently expressed in each of the 32 cell lines, thus U6 RNA is an acceptable internal control for quantitative PCR in these cell lines.

Figure 14:
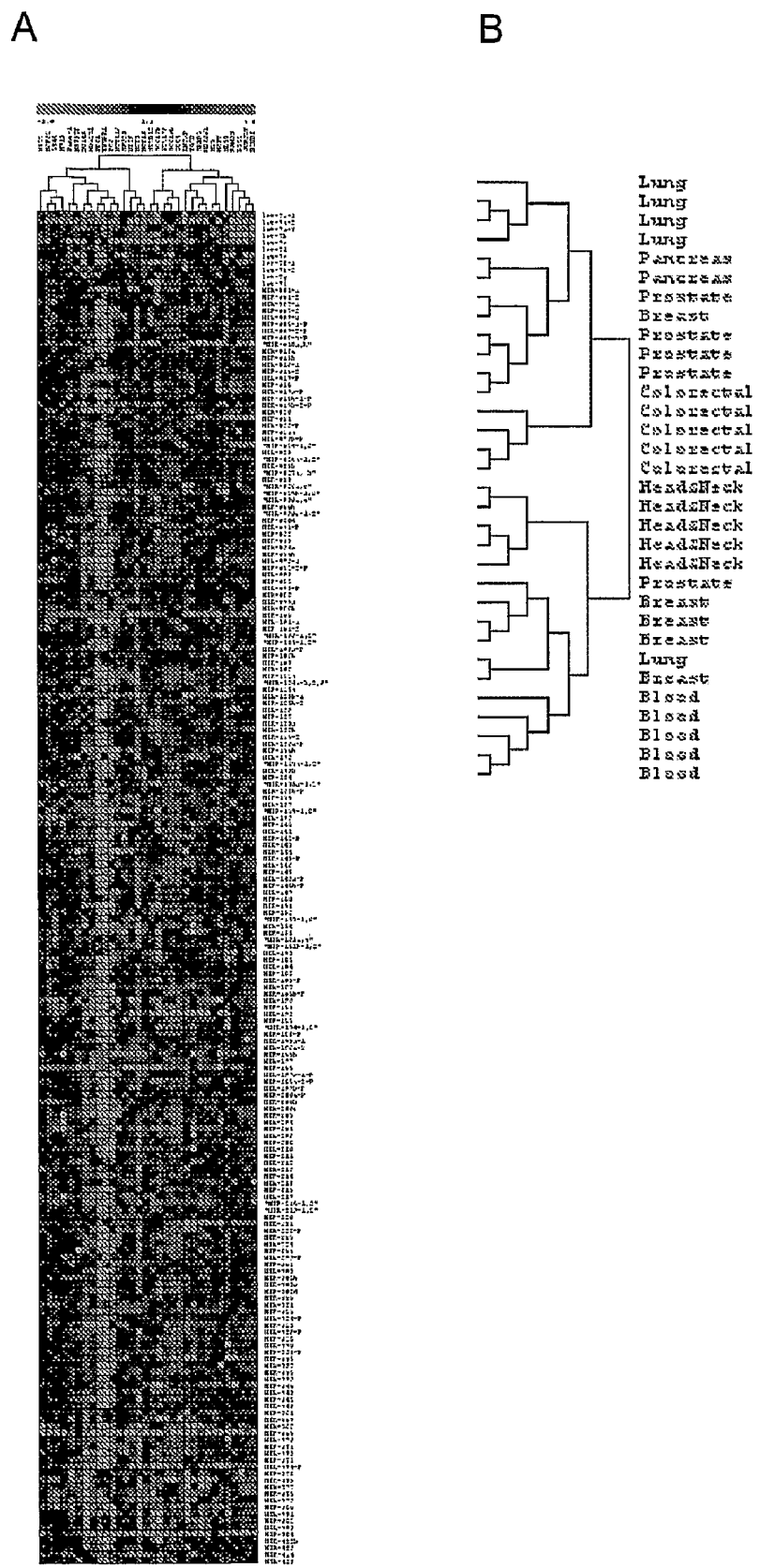
FIG. 14. Heatmap of miRNA precursor expression in 32 human cancer cell lines. The names of the 32 cancer cell lines are listed on the top of the figure. The names of the miRNAs that were profiled in the cancer cell lines are listed to the right of the figure. The relative expression of each gene was determined by real-time PCR; data are presented as ΔCT. Unsupervised hierarchical clustering was performed using PCR primers to 201 miRNA precursors. Data were unfiltered prior to clustering. A median expression value equal to one was designated black; red increased expression; green, reduced expression; gray, undetectable expression. (B) Dendrogram of clustering analysis.

The relative expression was determined for each of the 222 miRNA precursors. The relative expression for all 222 miRNA precursors was clustered using unsupervised hierarchical clustering and presented as a heatmap (FIG. 14). Unsupervised hierarchical was performed on the data presented as ΔCT. The heatmap and dendrogram demonstrate that most of the cell lines clustered into their respective tissues from which each cell line was ostensibly derived (FIG. 14). Five of five hematopoietic and head & neck cell lines and two of two pancreatic cell lines produced unique clusters. Four of five lung and colorectal cell lines produced unique clusters as well. The breast cancer and prostate cancer cell lines tended to cluster together with 4 of 5 of the prostate cell lines forming a cluster (along with one breast cancer cell line) and 3 of 5 breast plus one prostate forming another cluster (FIG. 14B).

Full details of the presented EXAMPLE 4 is provided in Jiang, J, Lee, E J, Gusev Y and Schmittgen T, Real-time expression profiling of microRNA precursors in human cancer cell lines, Nucleic Acid Research, 33(17):5394-5403 (2005), the contents of which are incorporated herein by reference.

What is claimed is:

1. A method for identifying the expression of both pri-microRNA and pre-microRNA precursors in a sample, said method comprising the initial step of using a gene-specific reverse primer to reverse transcribe a target nucleotide sequence, wherein the target nucleotide sequence comprises a substantial portion of a hairpin sequence shared by both the pri- and the pre-microRNA and the primer binds substantially within the hairpin sequence with no more than 4 nucleotides of the primer binding outside of the hairpin sequence.

2. The method of claim 1, further comprising:
   (a) subjecting the target nucleotide sequence to an amplification reaction to produce amplification products, wherein the amplification reaction uses a pair of gene specific primers that bind substantially within the hairpin sequence with no more than 4 nucleotides of either primer binding outside of the hairpin sequence, targeted to the target nucleotide sequence; and
   (b) detecting the amplification products.

3. The method of claim 1, wherein the target nucleotide sequence comprises the entire hairpin sequence.

4. The method of claim 1, wherein the target nucleotide sequence comprises nucleotides outside the hairpin sequence.

5. The method of claim 2, wherein the amplification reaction is a polymerase chain reaction (PCR).

6. The method of claim 2, wherein the amplification products are detectably labeled during performance of the amplification reaction.

7. The method of claim 6, wherein the detectable label is a fluorophore.

8. The method of claim 2, wherein the amplification reaction is an in-situ polymerase chain reaction (PCR) performed on tissues or cells.

9. A method for identifying differential expression of a microRNA precursor in a test sample, wherein the microRNA precursor comprises a hairpin sequence and said hairpin sequence comprises a mature microRNA sequence, said method comprising:
   (a) performing an amplification reaction on the test sample using one or more primers that bind substantially within the hairpin sequence and no more than 4 nucleotides of the primer bind outside of the hairpin sequence to amplify a target nucleotide sequence, said target nucleotide sequence comprising a portion of the hairpin sequence that is longer than the mature microRNA sequence;
   (b) detectably labeling the target nucleotide sequence;
   (c) detecting a difference between the amount of the detectably labeled target nucleotide sequence present in the sample relative to a corresponding mature miRNA control.

10. The method of claim 9, wherein the amplification reaction uses a reverse primer that is targeted to the 3' end of the hairpin sequence and a forward primer that is targeted to the 5' end of the hairpin sequence, and wherein both primers bind substantially within the hairpin sequence with no more than 4 nucleotides of either primer binding outside of the hairpin sequence.

11. The method of claim 9, wherein the amplification reaction is a polymerase chain reaction (PCR).

12. The method of claim 9, wherein the amplification reaction is an in-situ polymerase chain reaction (PCR) performed on tissues or cells.

13. The method of claim 9, wherein the target nucleotide sequence is detectably labeled during performance of the amplification reaction.

14. The method of claim 9, wherein the amplified target nucleotide sequence is detectably labeled by a nucleic acid probe that is a fluorophore.

15. The method of claim 9, wherein the amplified target nucleotide sequence is detectably labeled by a double stranded DNA probe.

16. A method for detecting the expression of a pre-microRNA precursor in a biological sample containing the pre-microRNA precursor and its corresponding pri-microRNA precursor, wherein both the pri-microRNA and the pre-microRNA precursors comprise a common hairpin sequence, said method comprising:
  (a) subjecting the biological sample to a first amplification reaction to produce a first amplification product, wherein the amplification reaction comprises a first primer that binds substantially within the hairpin sequence with no more than 4 nucleotides of the primer binding outside of the hairpin sequence and a second primer targeted to a sequence at least a portion of which is upstream or downstream of the hairpin sequence;
  (b) detecting the expression level of the pri-microRNA precursor by detecting the first amplification product;
  (c) subjecting the biological sample to a second amplification reaction to produce a second amplification product, wherein the second amplification reaction uses a pair of primers targeted to non-overlapping portions of the hairpin sequence, wherein both primers bind substantially within the hairpin sequence with no more than 4 nucleotides of either primer binding outside of the hairpin sequence;
  (d) detecting the expression level of both the pri-microRNA precursor and the pre-microRNA precursor by detecting the second amplification product;
  (e) calculating the expression level of the pre-microRNA precursor by subtracting the expression level of the first amplification product from the expression level of the second amplification product.

17. The method of claim 16, wherein the first primer is a reverse primer targeted to the 3' end of the hairpin sequence and the second primer is a forward primer targeted to a sequence upstream of the hairpin sequence.

18. The method of claim 16, wherein the first primer is a forward primer targeted to the 5' end of the hairpin sequence and the second primer is a reverse primer targeted to a sequence downstream of the hairpin sequence.

19. The method of claim 16, wherein the pair of primers are targeted to the 5' end and the 3' end of the hairpin sequence, respectively.

20. A method of identifying the expression of first microRNA precursors in a sample, wherein said first microRNA precursors comprise a hairpin sequence, said method comprising:
  (a) subjecting the sample to an amplification reaction to produce amplification products using a pair of primers each targeted to non-overlapping primer sequences which are within or substantially within the hairpin sequence with no more than 4 nucleotides of either primer binding outside of the hairpin sequence;
  (b) detecting the amplification product with a detector probe.

21. The method of claim 20, wherein the detector probe binds to a nucleotide sequence that lies in between the non-overlapping primer sequences.

22. The method of claim 20, wherein the detector probe is a TaqMan probe.

23. The method of claim 20, wherein the sample contains a second microRNA precursor with substantially similar primer sequences to the primer sequences of the first microRNA precursor and wherein the detector probe binds only to the amplification products of the first microRNA precursor.

24. The method of claim 20, wherein the amplification reaction is PCR.

25. A method for detecting a first microRNA precursor in a sample that contains at least a second microRNA precursor that is an isoform of the first microRNA precursor, said first and second microRNA precursors further having hairpin sequences that contain substantially similar primer portions, said method comprising:
  (a) performing an amplification reaction on the sample to produce a first amplification product, containing the hairpin sequence of the first microRNA precursor, and a second amplification product containing the hairpin sequence of the second microRNA precursor, said amplification reaction using a forward primer and a reverse primer which both bind substantially within the hairpin sequence with no more than 4 nucleotides of either primer binding outside of the hairpin sequence and are targeted to substantially similar primer portions of the hairpin sequences of the first and the second microRNA precursors; and
  (b) detecting only the first amplification product using a sequence-specific detection probe targeted to a sequence that is unique to the hairpin sequence of the first microRNA precursor, wherein said unique sequence lies between the substantially similar primer portions of the hairpin sequences.

26. The method of claim 25, wherein the sequence-specific detection probe is a TaqMan probe.

27. The method of claim 1, wherein the primer binds only within the hairpin sequence.

28. The method of claim 1, wherein the primer has a length of from 16 to 24 nucleotides.

\* \* \* \* \*